US008560047B2

(12) United States Patent
Haider et al.

(10) Patent No.: US 8,560,047 B2
(45) Date of Patent: Oct. 15, 2013

(54) METHOD AND APPARATUS FOR COMPUTER AIDED SURGERY

(75) Inventors: Hani Haider, Center Lake, IA (US); O. Andres Barrera, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 770 days.

(21) Appl. No.: 11/764,505

(22) Filed: Jun. 18, 2007

(65) Prior Publication Data

US 2008/0009697 A1    Jan. 10, 2008

Related U.S. Application Data

(60) Provisional application No. 60/814,370, filed on Jun. 16, 2006, provisional application No. 60/827,877, filed on Oct. 2, 2006.

(51) Int. Cl.
*A61B 5/05* (2006.01)

(52) U.S. Cl.
USPC ............................................. 600/407; 606/45

(58) Field of Classification Search
USPC ............... 600/407, 424, 437, 471; 606/41, 45
See application file for complete search history.

(56) References Cited

U.S. PATENT DOCUMENTS

| | | | |
|---|---|---|---|
| 4,291,708 A | 9/1981 | Frei et al. | |
| 4,458,694 A | 7/1984 | Sollish et al. | |
| 4,668,087 A | 5/1987 | Strandell et al. | |
| 5,086,401 A | 2/1992 | Glassman et al. | |
| 5,617,857 A | 4/1997 | Chader et al. | |
| 5,682,886 A | 11/1997 | Delp et al. | |
| 5,792,147 A | 8/1998 | Evans et al. | |
| 5,880,976 A | 3/1999 | DiGioia, III et al. | |
| 5,882,206 A | 3/1999 | Gillio | |
| 5,921,992 A | 7/1999 | Costales et al. | |
| 5,987,960 A | 11/1999 | Messner et al. | |
| 6,002,859 A | 12/1999 | DiGioia, III et al. | |
| 6,205,411 B1 | 3/2001 | DiGioia, III et al. | |

(Continued)

FOREIGN PATENT DOCUMENTS

| | | |
|---|---|---|
| GB | 2147222 | 9/2008 |
| WO | 89/01192 | 2/1989 |

(Continued)

OTHER PUBLICATIONS

Haider et al., "Total Knee Replacement Bone Cutting Without Jigs: Is it Time?", 72$^{nd}$ Annual Meeting of the American Academy of Orthopaedic Surgeons AAOS, Washington, D.C., 2005.

(Continued)

*Primary Examiner* — Tse Chen
*Assistant Examiner* — Rochelle Reardon
(74) *Attorney, Agent, or Firm* — Shay Glenn LLP

(57) ABSTRACT

A number of improvements are provided relating to computer aided surgery. The improvement relates to both the methods used during computer aided surgery and the devices used during such procedures. Some of the improvement relate to controlling the selection of which data to display during a procedure and/or how the data is displayed to aid the surgeon. Other improvements relate to the structure of the tools used during a procedure and how the tools can be controlled automatically to improve the efficiency of the procedure. Still other improvements relate to methods of providing feedback during a procedure to improve either the efficiency or quality, or both, for a procedure.

31 Claims, 10 Drawing Sheets

(56) References Cited

U.S. PATENT DOCUMENTS

| | | |
|---|---|---|
| 6,285,902 B1 | 9/2001 | Kienzle, III et al. |
| 6,428,547 B1 | 8/2002 | Vilsmeier et al. |
| 6,450,978 B1 | 9/2002 | Brosseau et al. |
| 6,453,190 B1 | 9/2002 | Acker et al. |
| 6,497,134 B1 | 12/2002 | Faul et al. |
| 6,522,906 B1 | 2/2003 | Salisbury, Jr. et al. |
| 6,678,552 B2 | 1/2004 | Pearlman |
| 6,697,664 B2 | 2/2004 | Kienzle III et al. |
| 6,711,432 B1 | 3/2004 | Krause et al. |
| 6,757,582 B2 | 6/2004 | Brisson et al. |
| 6,827,723 B2 | 12/2004 | Carson |
| 6,837,892 B2 | 1/2005 | Shoham |
| 6,859,661 B2 | 2/2005 | Tuke |
| 6,892,090 B2 | 5/2005 | Verard et al. |
| 6,923,817 B2 | 8/2005 | Carson et al. |
| 7,166,114 B2 | 1/2007 | Moctezuma De La Barrera et al. |
| 7,213,598 B2 | 5/2007 | Zeiss et al. |
| 7,226,456 B2 | 6/2007 | O'Neil et al. |
| 7,302,288 B1 | 11/2007 | Schellenberg |
| 7,366,562 B2 | 4/2008 | Dukesherer et al. |
| 7,377,924 B2 | 5/2008 | Raistrick et al. |
| 2001/0034530 A1 | 10/2001 | Malackowski et al. |
| 2003/0069591 A1 | 4/2003 | Carson et al. |
| 2003/0153978 A1 | 8/2003 | Whiteside |
| 2003/0209096 A1 | 11/2003 | Pandey et al. |
| 2003/0229279 A1 | 12/2003 | Amstutz et al. |
| 2004/0015070 A1 | 1/2004 | Liang et al. |
| 2004/0043368 A1 | 3/2004 | Hsieh et al. |
| 2004/0106916 A1 | 6/2004 | Quaid et al. |
| 2004/0171924 A1* | 9/2004 | Mire et al. .................... 600/407 |
| 2005/0015005 A1 | 1/2005 | Kockro |
| 2005/0020909 A1 | 1/2005 | Moctezuma de la Barrera et al. |
| 2005/0131426 A1 | 6/2005 | Moctezuma de la Barrera et al. |
| 2005/0154296 A1 | 7/2005 | Lechner et al. |
| 2005/0156876 A1 | 7/2005 | Kong |
| 2005/0159759 A1 | 7/2005 | Harbaugh et al. |
| 2005/0228266 A1* | 10/2005 | McCombs .................... 600/414 |
| 2005/0288575 A1 | 12/2005 | de la Barrera et al. |
| 2006/0176242 A1 | 8/2006 | Jaramaz et al. |
| 2006/0241388 A1* | 10/2006 | Lavallee ...................... 600/416 |
| 2006/0293557 A1 | 12/2006 | Chuanggui et al. |
| 2008/0281989 A1 | 11/2008 | Hager et al. |

FOREIGN PATENT DOCUMENTS

| | | |
|---|---|---|
| WO | 00/63719 | 10/2000 |
| WO | 2004/001569 | 12/2003 |
| WO | 2004/069036 | 8/2004 |
| WO | 2005/000139 | 1/2005 |
| WO | 2005/007229 | 8/2005 |
| WO | 2007/056743 | 5/2007 |

OTHER PUBLICATIONS

Barrera et al., "Intra Operative Graphical Interface for Freehand Navigated Bone Cutting for TKR Without Jigs-Assessment of First Cuts", Poster 246, $5^{th}$ Combined Meeting of the Orthopaedic Research Societies of Canada, U.S.A., Japan and Europe, Banff, Alberta, Canada, 2004.

Haider et al., "Freehand Navigated Bone Cutting for TKR Without Jigs-Assessment of First Cuts", Poster 246, $5^{th}$ Combined Meeting of the Orthopaedic Research Societies of Canada, U.S.A., Japan and Europe, Banff, Alberta, Canada, 2004.

Barrera et al., "Freehand Navigation Cutting for Distal Femoral TKR bone for MIS", Annual Symposium of International Society for Technology in Arthroplasty (ISTA), Rome, Italy, 2004.

Haider et al., "Freehand Navigation Cutting for TKR Surgery Without Jigs: Simulation of Bone Saw Cutting", $4^{th}$ Annual Conference of the International Society for Computer Assisted Orthopaedic Surgery, CAOS-International, Chicago, IL, 2004.

Barrera et al., "Comparison of Distal Femoral TKR Bone Cuts by Freehand Navigation vs. Conventional Cutting Jigs", The Fourth Annual Conference of the International Society for Computer Assisted Orthopaedic Surgery, CAOS-International, Chicago, IL, 2004.

Forman et al., "Computer-Assisted Freehand Navigation for Knee Replacement Surgery", The Fourth Annual Conference of the International Society for Computer Assisted Orthopaedic Surgery, CAOS-International, Chicago, IL, 2004.

Haider et al., "Computer Simulation of Bone Cutting for Knee Replacement Surgery With Freehand Navigation", SE042, 71st Annual Meeting, American Academy of Orthopaedic Surgeons (AAOS), San Francisco, CA, 2004.

Haider et al., "Real-Time Simulation of Bone Cutting Minimally Invasive Knee Replacement Surgery", Podium paper No. 1618, International Society for Technology in Arthroplasty (ISTA), San Francisco, CAI Sep. 2003.

Piltner et al., "Computational Modelling of Novel Implants for Minimally Invasive Knee Replacement Surgery", Poster presented at the 16th Annual Nebraska Biomedical Research Workshop, Omaha, NE, Apr. 2003.

Barrera et al., "Simulation and Navigation for Knee Replacement Surgery", Paper presented at the $16^{th}$ Annual Nebraska Biomedical Research Workshop, Omaha, NE, Apr. 2003.

Brisson et al., "Precision Freehand Sculpting of Bone", CAOS International, Spain, 2003.

Barrera et al., "Comparison of Distal Femoral TKR Bone Cuts by Freehand Navigation vs. Conventional Cutting Jigs", CAOS International, Chicago, IL, 2004.

Richter et al, "Integration of Computer-Based Systems in Foot and Ankle Surgery", Navigation and MIS in Orthopedic Surgery, Ch. 63, Dec. 20, 2006, 11 pages.

* cited by examiner

| SURFACE ROUGHNESS (R) | + | − | + | + | + |
|---|---|---|---|---|---|
| IMPLANT FIT ERROR (F) | + | + | + | − | + |
| IMPLANT LOCATION ERROR (L) | + | + | + | + | − |
| ACCURACY OF EACH PLANER CUT (P) | + | + | − | − | − |

METHOD AND APPARATUS FOR COMPUTER AIDED SURGERY

PRIORITY CLAIM

This application claims priority to U.S. Provisional Patent Application No. 60/814,370, filed Jun. 16, 2006 and U.S. Provisional Patent Application No. 60/827,877, filed Oct. 2, 2006.

FIELD OF THE INVENTION

The Present invention relates to the field of computer assisted surgery. Specifically, the present invention relates to various aspects of a surgical suite in which a computer provides guidance or assistance during a surgical procedure.

BACKGROUND

Many surgical procedures are complex procedures requiring numerous alignment jigs and intricate soft tissue procedures. Preparing and placing the alignment jigs and other preparation is often a significant part of the procedure. For instance, when performing a total knee replacement procedure ("TKR"), the prosthesis must be accurately implanted to ensure that the joint surfaces are properly aligned. If the alignment is inaccurate, the misalignment will lead to failure of the joint, requiring the complex task of replacing one or more portions of the knee prothesis.

To ensure that the prosthesis is accurately implanted, during a TKR procedure, the surgeon uses a variety of jigs to guide the cutting of the femur and the tibia. The jigs are complex devices that require significant time to install on the patient during the surgical procedure.

The advent of computer assisted surgery provides the promise of simplifying many of the complexities of surgical procedures. In some instances, the computer may be used to guide the surgeon during the process. Although computer assisted surgery holds promise, there are numerous aspects to be addressed to make a system commercially viable. For instance, in addition to improving the efficiency of the procedures, the quality of the resulting procedures should be addressed. Accordingly, there continues to exist numerous aspects of computer assisted surgery that require improvement to improve the efficiency and/or quality of the procedure. The end result will encourage medical professionals to migrate toward computer assisted surgical systems.

SUMMARY OF THE INVENTION

In light of the foregoing, a computer assisted surgical suite having a number of improvements is provided. For instance, a surgical suite having a computer and a surgical tool that communicates with the computer may be provided. The system also includes a tracking element for tracking the position of the surgical tool. In one aspect, the system allows the surgeon to perform a surgical procedure on a virtual model of the patient using the surgical tool. As the surgeon performs the procedure on the virtual model, the computer stores the information regarding the sequence of the steps performed and the position of the surgical tool during the procedure. Once the surgeon is satisfied with the results on the virtual model, the stored information can be used during the procedure to assist or guide the surgeon.

According to a further aspect, the computer controls operation of the surgical tool in response to information detected regarding the surgical tool. For instance, the system may track the position of the surgical tool relative to the patient. Based on the data regarding the position of the surgical tool, the computer may send signals to the surgical tool to control the operation of the surgical tool, such as reducing the speed on the tool or turning the tool on or off.

According to another aspect, the system provides a communication link between the surgical tool and the computer system that allows the surgical tool to control operation of the computer system and the computer system to control operation of the surgical tool.

Another aspect of the system is directed toward the use of the surgical tool in a free hand procedure to reduce or eliminate the use of jigs during a procedure. In such a procedure, the computer tracks the position of the surgical tool relative to the patient and displays the results on a screen to guide the surgeon in the procedure. In a resection procedure, the system may be configured to identify the patient tissue with different colors to identify the proximity of the tissue to the resection boundaries. For instance, tissue that is not to be resected may be illustrated in a red color, so that the surgeon can easily see that the tissue is not to be resected. Tissue that is to be resected may be illustrated in a green color. Further, tissue at the boundary of the portion to be resected may be illustrated in yellow, so that the surgeon can easily see that the cuts are getting close to the boundary.

Yet another aspect of the system is directed toward improving the display of information during a surgical procedure. Specifically, depending on which portion of a procedure is being performed, the surgeon may desire to change the view of the information being displayed. It can be cumbersome to change the view in the middle of a procedure to a different view. Accordingly, the system can be used to automatically switch to a particular view based on the position of the surgical tool. Additionally, the surgeon may program this information before a procedure, or the system can learn to recognize that a particular surgeon desires a particular view based on inputs from the surgeon during various procedures.

According to a further aspect, the system provides a method for assessing and improving the quality of a bone cut. For instance, the system measures various parameters relating to the quality of a bone cut, such as surface roughness, accuracy of each cut. If the parameter fall within pre-defined limits, the system indicates to the surgeon that the resection was successful, so that the prosthesis can be implanted. If one or more parameter falls outside the pre-defined limits, the system may calculate the step or steps necessary to correct the bone cuts so that the surgeon can perform the necessary correction.

Another aspect of the invention is directed improving the monitoring of the surgical tool. For instance, in certain aspects of computer assisted surgery, the position of certain surgical tools may be quite important in assessing the steps necessary during the procedure. However, during the procedure, operation of the surgical tool may cause the tool to deflect. The deflection may result in the system misidentifying the actual position of the surgical tool. Accordingly, the present system may include one or more sensors for detecting deflection of a portion of the surgical tool and an element for modifying the tracking element in response to the detected deflection.

A still further aspect of the present invention is directed to a marker that is used for marking tissue to be resected. The marker includes an actuator that responds to signals from the computer system. A tracking element provides data to the computer regarding the position of the marker. Based on the position of the marker, the computer controls the marker between an extended position and a retracted position. Specifically, if the computer detects that the marker is on a portion of the patient that is to be marked, then the computer controls the marker to extend the marker to the extended position so that a tip of the marker is exposed to mark the patient. Alternatively, if the marker is on a portion of the patient that is not to be marked, the computer controls the marker to retract the tip of the marker so that the marker cannot mark the patient.

The foregoing and other aspects of the present invention are described in greater detail in the detailed description.

DETAILED DESCRIPTION OF THE INVENTION

Figure 1:
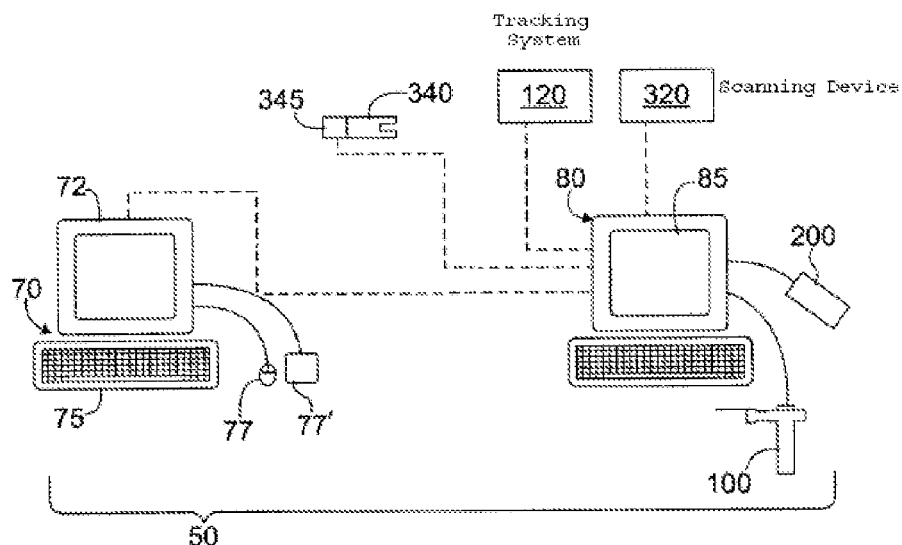
FIG. 1 is a diagrammatic view of a computer assisted surgical suite.

Referring now to the figures, wherein like elements are numbered alike throughout, a surgical suite for computer assisted surgery is designated generally 50. The suite 50 includes a first computer 70 for pre-operative use. For example, pre-operative analysis of the patient and selection of various elements may be performed on the first computer. The suite may also include a second computer 80, referred to as the OR computer, which is used during a procedure to assist the surgeon and/or control one or more surgical instruments. In addition the suite may include a computer (standalone or collaborating with 80) mounted on the surgical instrument. First computer 70 is provided in the present instance, but may be omitted in some configurations because the functions of computer 70 are also implemented on OR computer 80, which can be a standalone. Moreover the whole 'pre-surgical planning' may eventually happen instantaneously inside the OR. Nevertheless, if desired for particular applications, first computer 70 may be used. Furthermore, the micro-processing system of the system 50 can reside in the cutting instrument. In such a configuration, the computations and user interface can be performed within a computer on the surgical tool. Such system performs error analysis of location of the cutting instrument relative to the ideal cut to be performed, and displays corrective actions and other information on a screen mounted to the instrument.

The suite 50 may include a tracking/navigation system that allows tracking in real time of the position in space of several elements, including: (a) the patient's structures, such as the bone or other tissue; (b) the navigable surgical tools, such as the bone saw 100, which is controlled by the surgeon based on information from the OR computer 80 or (c) surgeon/assistants system specific tools, such as a pointer, registration tools, or other objects. The OR computer 80 may also perform some control on the cutting instrument trough the implemented of the present configuration of the system. Based on the location of the tool, the system 80 is able to vary the speed of the surgical tool 100 as well as turn the tool off to prevent potential damage. Additionally, the suite 50 may also include a surgical robot 200 that is controlled by the OR computer 80. The features of the navigable tool 100 and the surgical robot 200 may vary. The details of several desirable features are described in greater detail below. The various features can be selected as desired for a particular practice or situation. In the following description, the only surgical instrument shown in figures is the navigated saw 100. Nonetheless, many others instruments can be controlled and/or navigated as explained above, such as a drill, burr, scalpel, stylus, or other instrument. Therefore in the following discussion, the system is not limited to the particular tool described, but has application to a wide variety of instruments.

As discussed further below, one exemplary use of the surgical suite incorporates the use of a virtual model of the portion of the patient upon which a procedure is to be performed. Specifically, prior to a procedure, a three dimensional model of the relevant portion of the patient is produced using CT scans, MRI scans or other techniques. Prior to surgery, the surgeon may view and manipulate the patient model to evaluate the strategy for proceeding with the actual procedure.

One potential methodology uses the patient model as a navigation device during a procedure. For instance, prior to a procedure, the surgeon may analyze the virtual model of a portion of the patient and map out the tissue to be resected during a procedure. The model is then used to guide the surgeon during the actual procedure. Specifically, during the procedure a tracking mechanism monitors the progress of the procedure and the results are displayed in real time on the OR computer 80 so that the surgeon can see the progress relative to the patient model.

To provide navigation assistance during a procedure, the system 50 includes a position detection device 120 that monitors the position of the surgical tool 100. The surgical tool 100 includes one or more position markers 105 that identify pre-defined points of reference on the tool. In the present instance the surgical tool includes several markers 105 which, together with some pre-defined points of reference on the tool, identify the tool and its location.

Although a variety of position tracking systems can be used, one exemplary system is the NDI Polaris optical measurement system produced by Northern Digital Inc. The system uses a position sensor and both active and passive markers. The active markers may be wired sensors that are electrically connected to the system. The active markers emit infrared light that is received by the position sensor. The passive markers are wireless markers that need not be electrically connected to the system. The passive markers reflect infrared light back to the position sensor. Typically, when using passive markers, the position sensor floods the field of view with infrared light that is then reflected back to the position sensor from the passive markers. The position sensor includes an infrared receiver and it receives light emitted light from the active markers and reflected light from the passive markers. The position system triangulates the three dimensional position of the tool based on the position of the markers. In the present instance, the position detection device 120 is also operable to detect the orientation of the tool relative three orthogonal axes. In this way, the position detection device 120 determines the location and orientation of the tool 100.

The position detection device 120 is linked with the OR computer 80 so that the data regarding the position of the surgical tool 100, the patient's anatomy, and other system specific tools, is communicated to the OR computer. The computer uses this information to track the progress of a procedure.

Figure 4:
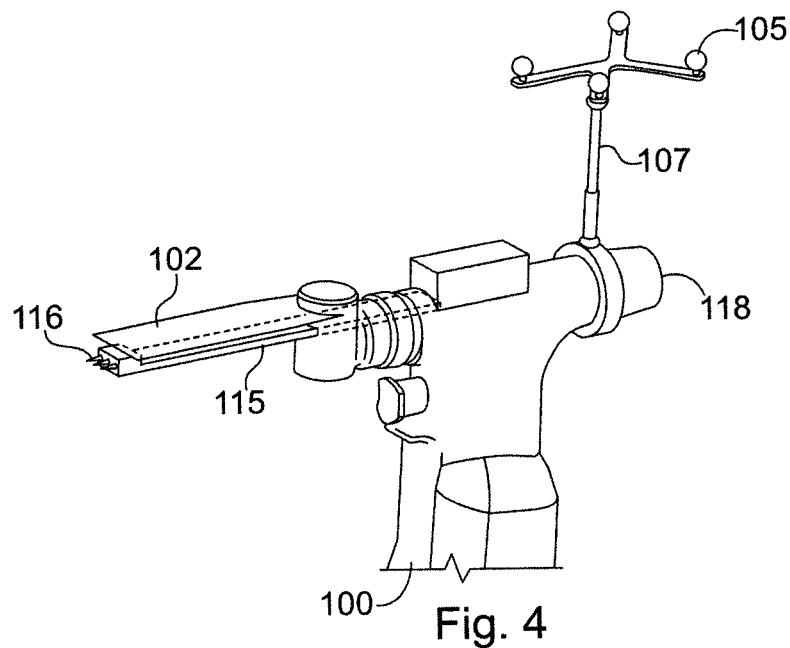
FIG. 4 is a fragmentary view of a surgical tool of the surgical suite of FIG. 1.

To track the position of the surgical tool 100 relative to the patient, position marker is attached to the portion of the patient on which the procedure is to be performed. The position marker attached to the patient may be similar to the position marker 105 attached to the surgical tool 100, as shown in FIG. 4. The position marker on the patient is correlated to a corresponding point on the virtual model of the patient. In this way, the registration point positions the tool relative to the patient and the patient relative to the virtual model.

A series of points are used to register or correlate the position of the patient's anatomy with the virtual model of the patient. To gather this information, a navigated pointer is used to acquire points at an anatomical landmark or a set of points on a surface within the patient's anatomy. A process referred to morphing may be used to register the patient to the virtual model of the patient. During such a process, the surgeon digitizes parts of the patient and some strategic anatomical landmarks. The computer 80 analyzes the data and identifies common anatomical features to thereby identify the location of points on the patient that correspond to particular points on the virtual model.

Accordingly, as set forth above, the position detector monitors the position of several items in real time, including: the position of the surgical tool 100, the position of the patient and the position of items used during a procedure, such as a pen or marker as described further below. Accordingly, the computer combines the data regarding the position of the surgical tool 100, the data regarding the position of the patient, and the data regarding the model of the patient. This combination is used to provide a real time model of the position of the tool relative to the patient, which can be viewed by the surgeon on the monitor. Further still, as previously described, prior to a procedure, the surgeon may analyze the patient model and identify the tissue that is to be resected. This information can then be used during the procedure to guide the surgeon.

During the procedure, the monitor displays a model of the surgical tool relative to the patient model, which reflects the real time position of the tools, such as the surgical tool 100, relative to the patient. The surgeon can align the position of the tool 100 by viewing the position of the image of the tool relative to the patient model on screen. Once the monitor shows the virtual tool to be aligned with the portion of the patient model identified for resection, the surgical tool is properly aligned on the patient. In this way, the doctor can align the tool without the need for complex jigs or fixtures. Further, as the tool 100 intersects the patient, the data regarding the position of the tool and the patient model is correlated to show the result of the tool intersecting the patient. In this way, the computer can analyze and display the progress of a procedure in real time. As the tool 100 cuts patient tissue, the monitor displays the tissue being removed from the patient model. Therefore, in addition to guiding the position of the tool, the OR computer can be used to guide the surgeon as to what tissue should be resected during a procedure.

In addition to including a surgical tool controlled by the surgeon, the suite 50 may include a surgical robot 200. The surgical robot can be programmed to perform one or more operations during a medical procedure. The surgical robot 200 is controlled by the OR computer, which is programmed with the instruction set for the procedure. As with the navigation system described above, when using the robot, the position detection device 120 monitors the position of the surgical robot, and prior to the procedure the location of the patient is identified so that the computer has data regarding the position of the surgical robot relative to the position of the patient.

Assessing and Correcting Bone Cuts

When implanting a prosthetic onto a bone, the surgeon must resect portions of the bone to prepare the bone to receive the prosthetic. Regardless of how the resection is performed, it is important to assess the quality of the cuts performed during a procedure prior implanting the prosthetic. Bad fit between the bone and the prosthetic causes a significant number of implant failures. Therefore, a close match between the shape and dimensions of the prepared bone and the prosthetic is important to the proper affixation and durability of the implant. The surgeon may rely upon experience and trial and error during a procedure, however, doing so does not provide a quantifiable method for ensuring that a resection is proper.

Accordingly, it may be desirable to incorporate a method and apparatus for assessing the quality of bone cuts before a prosthetic is implanted. Additionally, after assessing the bone cuts, it may be desirable to provide feedback regarding any additional shaping that should be made to improve the bone cuts to prepare the bone to receive the implant.

The steps for assessing and correcting bone cuts will not be described. First, the bone is resected according to the geometry of the prosthetic to be implanted. The resected bone is then scanned in three dimensions or digitized to obtain a three dimensional image of the bone. The scanned geometrical image is then analyzed to evaluate various criteria of the bone cuts. Based on the analysis of the scanned image, suggestions may be provided to the surgeon directly in the operating room before the prosthesis is implanted. In this way, the system provides feedback to the surgeon to allow for additional modifications to be made to the resected bone to improve the fit with the prosthesis.

Referring to FIG. 1, the system for assessing the bone cut comprises a scanning device 320 that communicates with a processor, such as a personal computer, which may be the OR computer 80. The processor communicates with an output device, such as a monitor 85 to illustrate information about the assessment of the bone cuts.

The scanning device 320 may be one of a number of various devices for acquiring information regarding the three dimensional configuration of an object. The scanner may use electromagnetic, ultrasonic/acoustic, mechanical, infra-red line-of site, or other elements. For instance, a three dimensional optical laser scanner, scriber, navigated digitizer, coordinate measuring machine or CT-based digitization can be used to create a digital model of the bone surface.

The processor analyzes the scanned data to evaluate each cut of the resected bone. For instance, in the case of a TKR procedure, there are typically five separate cuts made to the femur when the bone is resected to accommodate the prosthetic (it may be considered seven cuts rather than five when considering the posterior condyle resection as two cuts, as well as the posterior chamfer). The image data for the resected bone is analyzed to assess the surface finish for each of the five cuts. During the evaluation of the image data, the processor may evaluate several characteristics, including, but not limited to, surface finish, fit error (i.e. looseness), location error (alignment error), and the accuracy of each cut. Each of these characteristics is discussed below in greater detail.

Figure 7:
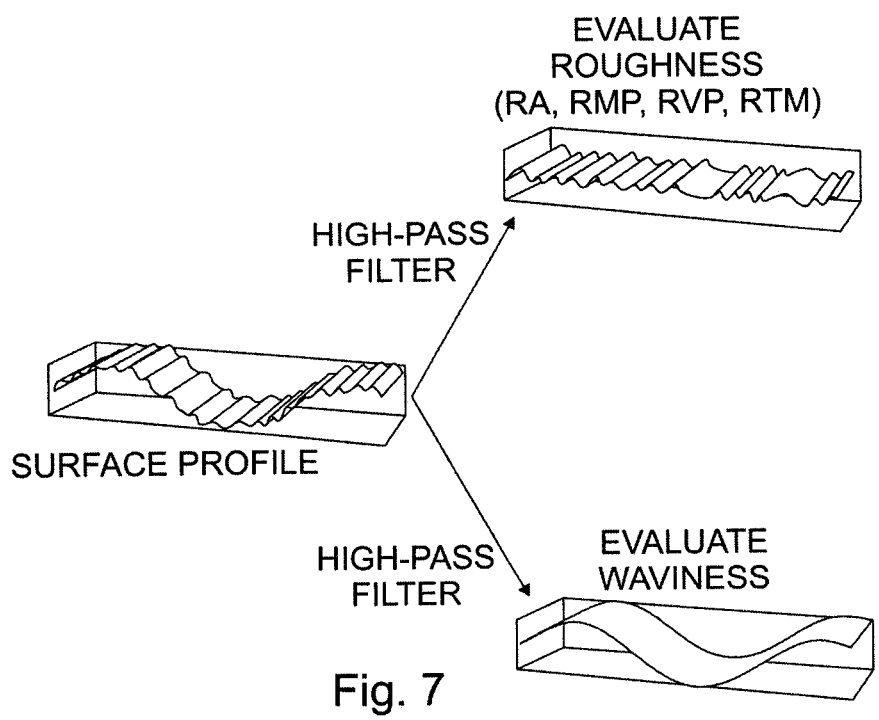
FIG. 7 illustrates a separation of the surface waviness and surface roughness of a surface profile.

Surface finish may include one or more characteristics to evaluate whether the surface is of sufficient quality to bond well with the prosthetic. In the present instance, the system analyzes the roughness and/or the waviness of the resected surface to assess the surface finish. Roughness includes the finer irregularities of a surface that generally result from a particular cutting tool and material conditions. Waviness includes the more widely spaced deviation of a surface from the nominal or ideal shape of the surface. Waviness is usually produced by instabilities, such as blade bending, or by deliberate actions during the cutting process. As illustrated in FIG. 7, waviness has a longer wavelength than roughness, which is superimposed on the waviness.

Figure 8:
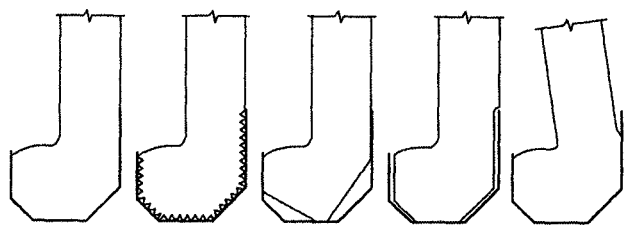
FIG. 8 is a table illustrating the various potential error in fitting an implant.
Figure 9:
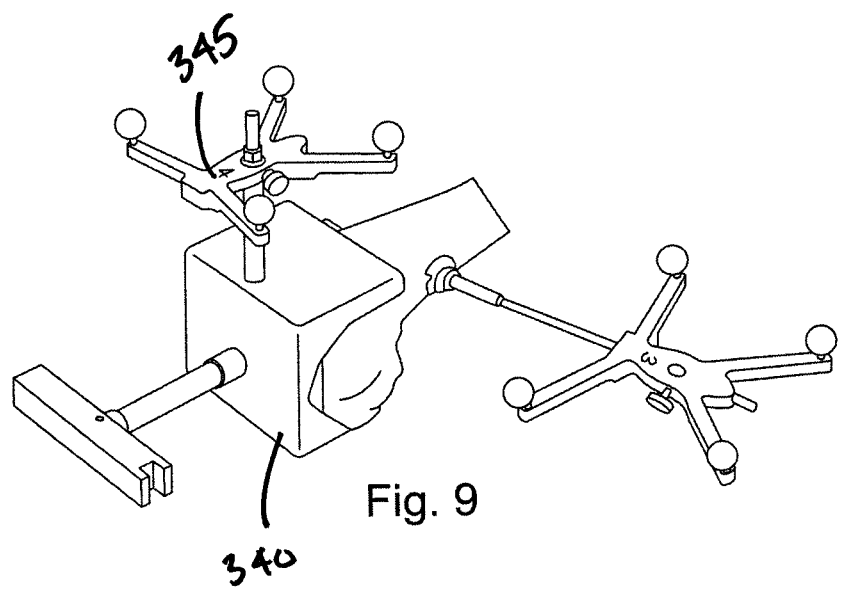
FIG. 9 is a measuring block for assessing the fit of an implant.

Based on analysis of the 3D geometrical image data, the surface finish for each cut is analyzed and quantified. In the present instance, the surface finish may be quantified based on: (1) the roughness average, (2) an average of the heights of a select number of the worst peaks (i.e. highest surface peak relative to ideal surface); (3) an average of the heights of a select number of the worst valleys (i.e. deepest valley relative to ideal surface); and (4) a measure of the deviation from the average height of the worst peaks and the average depth of the worst valley (i.e. (2)-(3)). In some instances, it may be desirable to separate the quantification of the measure of waviness from the measure of roughness. However, in the present instance, roughness and waviness are evaluated together. An example of a resected femur having unacceptable surface finish is illustrated in FIG. 8. As can be seen, the geometry of the resection is proper, so that the prosthetic would fit properly onto the resected bone and be properly aligned. However, due to the poor surface finish it is likely that the bond between the bone and the prosthetic will fail prematurely.

In addition to surface finish, it is desirable to analyze the fit error of resected bone. Fit represents the looseness or play between the implant and the resected bone shape prior to affixing the prosthetic to the bone. An example of a resected femur having an unacceptable fit error is illustrated in FIG. 8. As can be seen, the surface of each cut is acceptable and the orientation of each cut is acceptable, however, the resultant shape leaves unacceptable gaps between the prosthetic and the resected bone. The gaps create play or looseness that will lead to misalignment and/or premature failure of the bond between the bone and the prosthetic.

To measure the fit error, a fitness measuring block 340 may be utilized. The fitness measuring block 340 is a block having an internal shape corresponding to the internal shape of the prosthetic (i.e. the surface that will bond with the bone). A sensor 345 for detecting displacement is attached to the fitness measuring block. In the present instance, the sensor is an infrared tracking device. Alternatively, a navigated implant trial that is specific to each prosthetic implant may be used rather than a measuring block. The navigated implant trial is an implant similar to the prosthetic that is to be implanted into the patient. The navigated implant includes an element for detecting the position of the implant trial, such as the sensor 345 described above. The tracking device 120 (see FIG. 1) tracks the position of the tracking sensor 345 and communicates data to the processor that is indicative of displacement of the fitness measuring block relative to the resected bone.

The measuring block 340 is placed over the resected bone. The surgeon then attempts to move the measuring block in all directions relative to the bone to evaluate translational error based on the amount of translation possible between the measuring block and the resected bone. Specifically, the surgeon rotates the block in flexion and extension, as well as internally and externally. In other words, the surgeon rotates the blocks about several axis relative to the bone, such as an axis running generally parallel to the axis of the bone (i.e. rotation internally and externally) as well as an axis running generally transverse the axis of the bone (i.e. rotation in flexion and extension). As the surgeon moves the measuring block, the sensor detects the translational and rotational movement relative to the bone and communicates the data with the processor (such as OR computer 80). Based on the data from the sensor 345 and/or position detection element 120, the processor analyzes and quantifies the fit based on the measured translational error and the measured rotational error.

A third characteristic for assessing the cuts is the location of the cuts, which is the location that the implant may be positioned. The third parameter relates to error of the final position case of a tight fit or minimum possible error in case of looseness after the bone is cut and before the prosthetic is cemented. The assessment is performed using the same data set that was collected while analyzing the implant fit as described above.

The location error is quantification of the deviation of the location of the measuring block from the ideal location at which the implants are to be positioned. Specifically, in the present instance, the location error is based on three rotational deviations and three translational deviations from the ideal locations. In the case of the trial stage, before drilling the holes for the stems of the implant, only two translational errors are considered. The holes are drilled to accommodate one or more alignment stems that are located on the interior of the implant. Once the holes are drilled, the holes constrain the position of the implant relative to the patient. Accordingly, prior to drilling the holes it may be desirable to assess the cuts. After analyzing and/or modifying the cuts, the system may be used to guide the holes to be drilled. As part of the assessment process, the measuring block is manipulated to account for medial and lateral deviation because of constraints in other directions. In this way, depending on the procedure being analyzed, the directions in which the block is manipulated may vary.

In the foregoing description, the evaluation of the location error and fit error are based on measurements provided by manipulating the fit measurement block 340 relative to the resected bone. Alternatively, the fit and location errors may be evaluated using a virtual comparison of the resected bone and models of ideal location and fit for the bone. For instance, as described above, the resected bone may be scanned to create a three dimensional model of the resected bone. Prior to the procedure a three dimensional model of the relevant portion of the patient can be created using any of a variety of techniques, including but not limited to CT scans and MRI images. The processor may include a database of models corresponding to various prosthetics. The surgeon selects the appropriate prosthetic model and positions it relative to the model of the relevant portion of the patient. The processor then modifies the patient model to reflect the ideal resected surfaces for the selected prosthetic. Using collision detection algorithms, the scanned data for the resected bone can be compared with the data for the model for the ideal resected bone to calculate the various criteria used to measure fit error and location error.

A final characteristic used in the present instance to evaluate the bone cuts is the accuracy of each cut. For example, in the instance of a TKR procedure, the accuracy of each cut is evaluated. The importance of the accuracy of the cuts is exemplified by the third sample illustrated in FIG. 8. As can be seen, the sample has acceptable surface finish, fit and location. In other words, the prosthetic will fit well on the bone (i.e. it won't wiggle excessively), the surface finish is not too rough or wavy and the prosthetic will be properly aligned with the bone. However, due to the inaccuracy in one or more of the cuts, there will be gaps between the prosthetic and the bone that will increase the likelihood of premature failure.

To evaluate the accuracy of the cuts, the deviation between the actual cuts and the ideal cuts for the particular prosthetic is measured. The ideal cuts are determined based on the geometry of the prosthetic to be implanted on the resected bone. For instance, in the example of a TKR, the ideal cuts for the femur are based on the internal configuration of the femoral prosthetic. One way of determining the ideal cuts is to create a model of the configuration of the ideal cuts for the patient, as described above As described above in connection with evaluating the surface finish, in the present instance, a scanner 320 (shown in FIG. 1) is used to create a model of the resected bone. The data obtained from the scanner 320 for each planar resected surface is compared with the data for the corresponding surface of the ideal resected model to evaluate the accuracy of the cuts. The quantification of the accuracy can be based on a variety of measurements regarding the deviation of each resected surface from the ideal surface. In the present instance, four characteristics are measured. The first characteristic is a translational measurement, and it is calculated as the distance between the plane of the resected surface to the centroid of the corresponding ideal cut. The remaining three characteristics are rotational angles. The first rotational characteristic is the orientation of the resected surface relative to the ideal plane with respect to a first axis; the second rotational characteristic is relative to a second axis and the third rotational characteristic is relative to a third rotational axis. These characteristics are measured and correlated to quantify the accuracy of each planar cut of the resected bone.

After the processor determines the various criteria to assess the quality of the cuts, the information regarding the criteria may be displayed on the monitor to indicate to the surgeon whether or not the cuts were of sufficient quality to proceed with implanting the prosthetic on the bone. Additionally, if the cuts are not of sufficient quality, the processor may evaluate the cuts to determine a strategy for modifying the resected bone to improve the quality of the cuts. For instance, based on a comparison of the scanned data for a resected bone with the data for the model of an ideal resected bone, the processor may determine the portion(s) of bone that should be re-shaped to improve the correlation between the resected bone and the model for the ideal resected bone. After determining the portions of the bone that should be re-shaped, such changes are displayed on the monitor to show the surgeon which portion(s) of the bone should be removed. For example, using a graphical output, the bone may be illustrated generally in white and the portion(s) of the bone that should be resected to improve the fit with the prosthetic may be shown in red.

In light of the foregoing, the method of assessing the quality of cuts for a procedure operates as follows. For in-vivo and in-vitro applications, a three dimensional model of a portion of a patient may be generated using any of a variety of three-dimensional digitizing, scanning and imaging techniques. The surgeon then selects the element to be inserted or implanted into the patient and the processor generates a model of the patient with the location and orientation of the ideal cuts to the respective portion(s) of the patient.

Programming Path for Surgical Robot

As discussed previously, the system provides feedback for a surgeon during a surgical procedure to aid in guiding the path that the surgeon should follow during a procedure. Additionally, it may be desirable to provide the ability to easily define the path that a robot should follow during a procedure.

Figure 12:
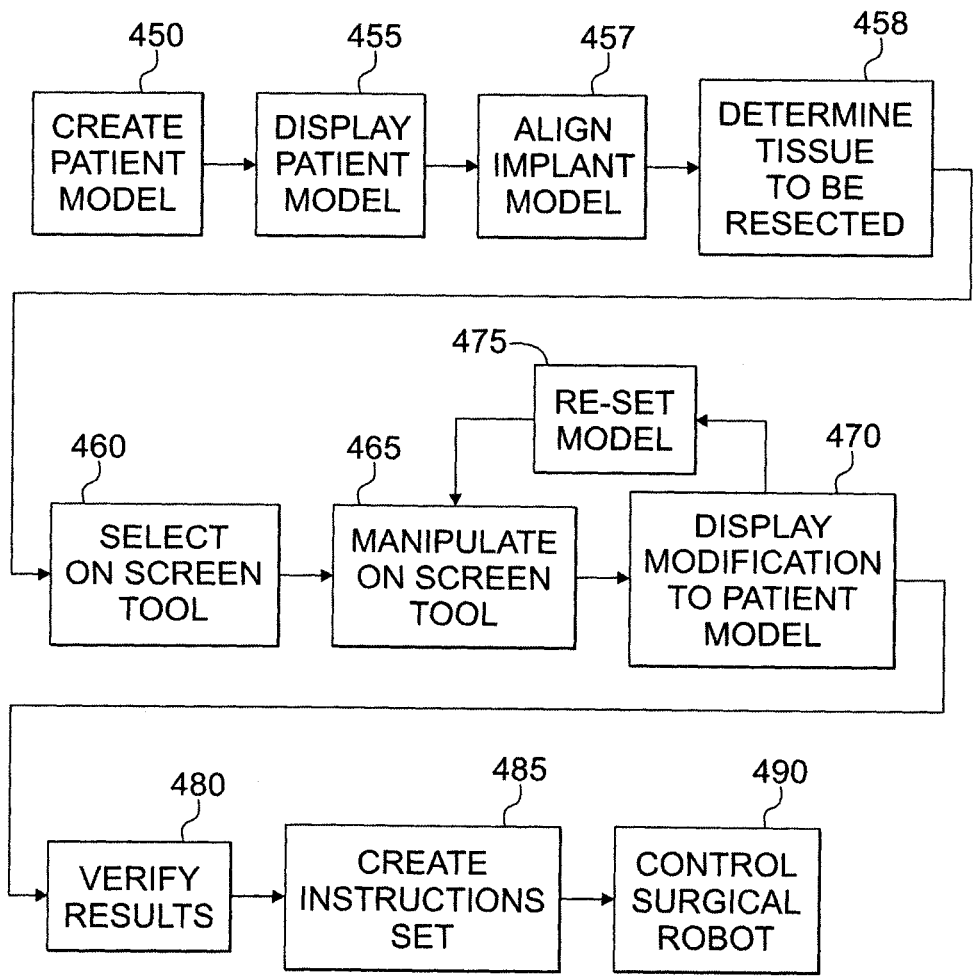
FIG. 12 is a diagram illustrating the steps of a method for programming a surgical robot.

Referring to FIGS. 1 and 12, a system for programming a surgical robot 200 is illustrated. To program the robot, a doctor performs a virtual procedure on a model of a portion of the patient. The virtual procedure is then translated into a set of instructions that the surgery robot follows during the actual procedure on the patient.

The system for programming the robot includes a virtual surgery computer, such as the pre-op computer 70 and a control computer, such as the OR computer 80. The control computer communicates with and controls the operation of the surgical robot 200. The virtual surgery computer is used to create the instructions for the surgery robot.

In step 450, a virtual model is created for the portion of the patient on which the procedure will be performed. As described above, a virtual model can be created using a series of CT scans, MRI scans, interpolating the data among the scans, using statistical procedures, directly digitizing a portion of the patient, or otherwise. The patient model is uploaded to the virtual surgery computer and is displayed to the surgeon in step 455.

The virtual surgery computer includes one or more input devices for inputting information into the computer. For instance, the computer may include a keyboard 75 and one or more position tracking devices 77 such a mouse or a stylus and pad.

Software on the virtual surgery computer allows the surgeon to manipulate and perform a virtual procedure on the patient model. Specifically, the software provides an interface so that the surgeon can manipulate the patient model to view the patient model from different angles and perspectives. For instance, the surgeon can use the keyboard alone or in combination with the mouse to manipulate the orientation of the patient model.

The system may also include the ability to virtually align and place an element that is to be implanted during the actual procedure. Further still, the location and amount of tissue to be resected may be calculated and displayed on the patient model.

During many surgical procedures, an element is implanted into the patient. For instance, during an orthopaedic procedure, a prosthetic element is implanted into the patient to replace one or more articular surfaces in a joint. One example is a total knee replacement (TKR) in which surfaces of the knee joint are replaced with a series of knee prosthetics. The procedure includes the placement of a patellar prosthetic onto the patella, a femoral prosthetic on the end of the femur and a tibial prosthetic on the tibial plateau. During the placement of each prosthetic, a portion of the corresponding bone is resected to accommodate the respective prosthetic.

During the actual procedure, the bone to be resected is determined by configuration of the prosthetics and the position and orientation of the prosthetics relative to the corresponding tissue. Accordingly, during the process of programming the surgical robot, it is desirable to utilize models of the prosthetics. Specifically, the virtual surgery computer may include three dimensional models representing the size and shape of various prosthetics.

To incorporate a model of a prosthetic into a virtual procedure, the surgeon selects a prosthetic and the size for the prosthetic. Typically, during an actual surgery, alignment jigs and fixtures are used to identify the bone to be resected. Similarly, during a virtual surgery the model is aligned to the bone (step 457). When performing a virtual surgery, the software may include alignment tools that are configured to identify relevant criteria on the tissue that is used to locate and align the virtual model of the prosthetic. In other words, the virtual alignment tools may operate to automatically align the model of the prosthetic based on a characteristic of the patient model. The characteristic can be automatically identified by the computer based on a set of pre-established criteria for evaluating a patient model, or the characteristic can be identified by the surgeon. After the relevant characteristic is identified, the alignment tool in the software is used to identify the location and orientation for the prosthetic model. Alternatively, the surgeon may manually align the model of the prosthetic onto the patient model based on the configuration of the prosthetic and the configuration of the patient.

After the location and orientation of an implant is determined, the computer may automatically determine the tissue to be resected (step 458). Specifically, the amount of tissue to be resected is determined based on the configuration of the prosthetic as known from the model, and based on the orientation and location of the prosthetic as determined during the alignment of the prosthetic described above. By way of example, when implanting a femoral prosthetic, the configuration of the prosthetic is known from the data for the prosthetic model. Once the model of the femoral prosthetic is aligned on the model of the patient, the computer can evaluate the intersection of the prosthetic model and the model of the patient's femur to determine the location and the amount of the femur that should be resected to accommodate the femoral prosthetic. This determination is then displayed on the patient model to aid the surgeon in the virtual surgery. For example, if the femur is displayed as a white solid object, the bone to be resected may be displayed as a red portion of the femur.

The software also includes onscreen tools that the surgeon can control via one or more of the position tracking devices 75, such as a surgical saw, a mouse or a pointing device. Further, preferably the software provides a number of different tools that the surgeon can select (step 460) during the virtual procedure. The onscreen tool can be as simple as a pointing device that allows the surgeon to trace a path along the patient model. The path represents the path that the surgeon desires the surgical robot to follow during the actual procedure. Further, the onscreen tools can be representative of tools that will be used during the actual procedure. For instance, the tools may include a cutting element, such as a bone cutting saw.

After selecting the appropriate onscreen tool, the surgeon manipulates the input device 77 to manipulate the onscreen tool relative to the patient model (step 465). The surgeon can manipulate both the position and the orientation of the onscreen tool relative to the patient model. As the onscreen tool is moved relative to the patient model, the software evaluates and displays the result (step 470). For instance, if the onscreen tool is a saw and the saw intersects the patient model, the software alters the patient model to show a portion of the patient model cut and/or removed.

Specifically, based on the coordinates provided by the input device 77, the software determines the position and orientation of the onscreen tool relative to the patient model. The software determines what portions of the onscreen tool and patient model intersect, and at what angle the tool intersects the patient model. If the onscreen tool intersects the patient model, the software determines the coordinates of the intersection and the result of the intersection based on the tool selected. For example, if the onscreen tool is a drill, the software will determine the size, location, angle and depth of the hole based on the diameter of the drill selected by the surgeon and the position of the drill relative to the patient model. The result of the intersection between the onscreen tool and the patient model is illustrated in real time (step 470) so that the surgeon can see the result of the virtual procedure as it is performed.

In this way, the surgeon can use a virtual surgical tool to perform a virtual procedure and the virtual surgery computer will display the progress of the procedure in real time. Further, if the tissue to be resected is identified on the model, as described above, the computer shows the removal of such tissue as it is virtually resected. For instance, in the example in which the bone to be resected is displayed in red, the computer will show the removal of the red portion of the bone, as the surgeon virtually operates on the bone.

The surgeon can reset the patient model to restart the virtual procedure so that the surgeon can see the result of using different paths (step 475). The surgeon can either re-set the entire procedure or just one or more of the steps taken during the virtual procedure. For instance, the surgeon can perform the surgical procedure along a first path or series of paths, and then perform the virtual surgery along a different path or series of paths to determine which path is the optimum path to use for the actual surgery. Additionally, since the surgical procedure will likely include a plurality of paths (i.e. more than a single cut), the surgeon can re-set a particular step rather than all of the steps in a virtual procedure. Specifically, if the surgeon performs a number of steps in a virtual procedure, the surgeon can re-set each step in series to step back through the procedure to alter one or more of the steps. For instance, after the seventh step the surgeon may be unhappy with the result, so the surgeon may undo the previous two steps. The software then resets the model so that it displays the result of the patient's model after the first five steps in the virtual procedure.

As described above, the surgeon performs a virtual procedure of one or more steps by manipulating an input device to control the path of one or more onscreen tool(s). After the surgeon is satisfied with the result of the virtual procedure, the surgeon verifies the virtual procedure to confirm that the virtual procedure is to be used to create the instructions for the surgical robot 200. The verification can be as simple as providing an input indicating that the virtual procedure performed is to be used to create the instructions for the surgical robot.

As described above, the virtual surgery computer monitors the input of the input device during the virtual procedure. At the same time, the computer records various information for each step of the virtual procedure. Specifically, for each step, the computer records the tool used, the path that the tool was displaced relative to the patient model, and the orientation of the tool relative to the patient model.

The path and orientation of the onscreen tool are determined relative to a reference point on the patient model. The reference point is used to correlate the patient model and the patient during the surgical procedure. In other words, the path and orientation of the onscreen tool for each step of a procedure is determined relative to the reference point, and then the path and orientation of the surgical robot are calculated to orient and displace the surgical robot relative to the reference point.

Based on the data recorded for each step of the virtual procedure, the computer calculates a series of instructions for the surgical robot. The instructions are exported to a server that is in communication with the control computer. The instruction set is then uploaded to the control computer to be used to control the surgical robot during a procedure.

To commence the actual surgical procedure, the position of the surgical robot is correlated with the reference point on the patient. After the position of the robot is correlated with the reference point on the patient, the surgeon commences operation of the surgical robot. The control computer controls the position and orientation of the surgical robot in response to the instruction set determined in step 485. In this way the movement of the tool on the surgical robot parallels the movement of the onscreen tool as manipulated by the surgeon during the virtual surgery. Specifically, based on the instructions set, the control computer controls the movement of the surgical robot tool, so that the displacement path and orientation of the surgical robot tool relative to the reference point is substantially similar to the displacement path and orientation of the onscreen tool relative to the reference point on the patient model. Further, the control computer controls the surgical robot so that the surgical robot follows the identical or substantially the same sequence of steps that the surgeon took during the virtual surgery. Specifically, the control computer controls the surgical robot so that the first step taken by the surgeon is the first step taken by the surgical robot; the second step taken by the surgeon during the virtual surgery is the second step taken by the surgical robot, and so on. In this way, the sequence of steps, along with the movement and orientation of the surgical robot tool is the same as or substantially similar to the sequence of steps, and the movement and orientation of the onscreen tool used by the surgeon during the virtual procedure.

In the foregoing description, the system has been described as including two separate computers connected with a server. The advantage of such a configuration is that the virtual surgery performed to program the surgical robot can be performed remotely from the operating area. However, the actual configuration of the system can vary. For instance, the virtual surgery computer can be directly linked to the control computer, eliminating the need for a server. Alternatively, rather than linking the two computers, data from the virtual surgery computer can be exported to a storage medium and then uploaded to the control computer. For instance, the data, such as the instructions set can be exported to a optical disk, such as a CD or other memory device, and the control computer may include a device for reading the data from the storage medium. Further still, it may be desirable to use a single computer for both the virtual surgery and to control the surgical robot, thus eliminating the need for two separate computers and a server. In addition, although the surgical robot has been described as being controlled by a separate computer, the robot may be controlled by an integrated microprocessor that receives the operating instructions and controls the robot, rather than a separate computer such as a personal computer.

Detecting Tool Deflection

As described above, the position detection device 120 can be used to detect and monitor the position of either a surgical tool 100 or a surgical robot 200. One issue in correctly navigating the surgical tool or the robot is the need for an accurate assessment of the position and orientation of the surgical tool or robot. Specifically, although a number of markers 105 may be used to identify the position of a tool, markers are typically not applied to the tip of a tool, particularly if the tool is a cutting tool. Instead, the position of the tool is determined and the position of the cutting tip is calculated based on the known geometry of the tool, and the presumption that the tool is a rigid element. However, during use, the tool may deflect or deform so that the actual position of the cutting tip may not correspond to the presumed position of the cutting tip. Therefore, the correlation between the actual tissue being cut and the virtual model do not match. In other words, based on the data received from the position detection device the OR computer 80 determines that a certain portion of tissue is resected, however, due to tool deflection the actual tissue resected may be different.

To accurately identify the position of a tool during a procedure, the tool may include a sensor for detecting deflection or deformation of the tool. For instance, referring to FIG. 2, a surgical tool 100 is illustrated, having a cutting blade 102. The surgical tool 100 reciprocates the cutting blade during operation. A sensor in the form of a load-cell 104 included in the saw detects the force and/or torque applied to the blade. Alternatively, a piezoelectric sensor may be connected directly to the blade to detect the force and/or torque applied to the blade. The measured force or torque is used to predict the distance "d" that the blade bends. Specifically, properties of the cutting blade 102 are stored. Based on the predefined cutting tool properties and the measured force or torque, the amount of bending is calculated. The calculated amount of bending approximates the distance "d" and is used as a compensation factor to adjust the position of the cutting tool detected by the position detection device 120.

In the embodiment discussed above, the position of the cutting tool is constantly calculated based on the measured position of the cutting tool and the measured amount of force or torque applied to the cutting tool. An alternative utilizes an onboard processor to calculate the tool deflection and manipulate the position detection element(s) on the cutting tool. In this way, the position detection device 120 will detect the compensated position of the cutting tool, which will reflect the actual position and orientation of the deflected cutting tool.

Referring again to FIG. 2, the surgical tool 100 may include a processor 106 operable to receive signals from the load cell 104 indicative of the force applied to the cutting blade. Based on the data received from the load cell, the processor 106 calculates the deflection "d" of the tip of the cutting tool 102.

Figure 2:
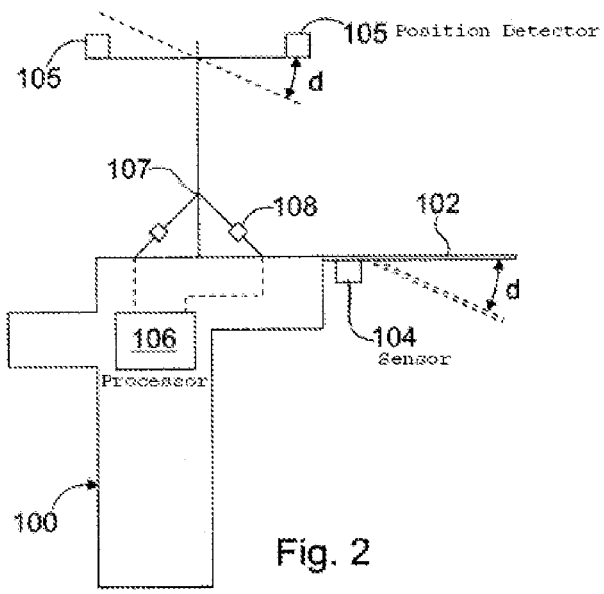
FIG. 2 is a diagrammatic view of a surgical tool of the surgical suite of FIG. 1.

As shown in FIG. 2, the surgical tool 100 includes an element for detecting the position of the surgical tool. For instance, in the present instance, the surgical tool includes a reference frame onto which a plurality of markers 105 are mounted. As described previously, the position detection device 120 detects the position of the markers to determine the location and orientation of the surgical tool.

In a system in which the deflection compensation is performed by either the position detection device or the OR computer, the frame is typically rigidly mounted to the surgical tool so that the position of the markers relative to the rest of the tool is fixed. However, as shown in FIG. 2, the frame 107 may be movably connected to the surgical tool 100. Although the freedom of movement of the frame may be limited, preferably the frame is connected to the surgical frame by a connection that provides at least two degrees of freedom, such as a universal joint.

Connected to the frame 107 are a plurality of actuators or deflectors 108 that control the position of the frame. The actuators 108 are in electrical communication with the processor 106, and preferably the processor 106 independently controls the operation of each actuator.

The processor 106 controls the operation of the various deflectors 108 based on the signals received from the sensor 104. Specifically, as described above, the processor 106 calculates the deflection "d" of the tip of the cutting tool based on the signal received from the sensor 104. Based on the calculated deflection, the processor determines the appropriate compensation to the position of the frame to compensate for the deflection of the cutting tool 102. The processor then controls the operation of the actuators 108 to re-position the frame. For instance, in the example illustrated in FIG. 2, the cutting tool is deflected an amount "d" in a clockwise direction. Accordingly, the actuators 108 reposition the frame 107 to displace the markers 105 an amount "d" in a clockwise direction. The position detection device 120 then detects the position of the surgical tool at the compensated position so that no further calculations are necessary to monitor the position of the deflected cutting tool.

By utilizing an on board deflection compensation, the system can incorporate deflection compensation, while still allowing the surgical tool to be used with a variety of commercially available position detection devices without the need to modify the software used by such devices.

Although the foregoing example describes the onboard compensation feature as utilizing a plurality of actuators to reposition a reference frame, the configuration of the compensation elements may vary depending on the configuration of the position detection elements used.

For instance, other position detection devices may be used in the system, such as systems that include electromagnetic sensors, ultrasound elements or accelerometers. When such elements are utilized, the compensation features may either vary the position of the element or it may vary the data provided by such elements in response to the data received regarding the load on the cutting tool.

Alignment Element for Surgical Tool

When performing a navigated freehand procedure as described above, one of the issues is the time that a surgeon typically takes to align a cut before starting the cut. Frequently this alignment causes unnecessary delay. To limit the delay caused during the alignment process, the surgical tool may includes an alignment guide mounted on the surgical tool. The position of the alignment guide 115 is known relative to the surgical tool, so that the position detection device 120 can determine the position of the alignment guide. Accordingly, using the virtual navigation, the surgeon can watch the monitor 85 (or a screen mounted on the instrument) to see the position of the blade relative to the target point for the cut identified on the virtual model. When the tool is properly aligned on screen, the tool is properly aligned on the patient. The guide is the anchored to the patient to align the tool for the cut.

Referring to FIG. 4, the alignment guide 115 is an elongated element positioned adjacent the cutting tool 102. The forward end of the alignment guide 115 is positioned so that the tip of the alignment guide protrudes beyond the tip of the cutting tool. In the present instance, the alignment guide 115 includes a plurality of retractable pins or spikes 116 positioned at the end of the guide. The pins 116 are configured to anchor the guide 115 into bone. The alignment guide 115 further includes a recess for receiving the pins 116 when the pins retract so that the pins do not interfere with the cutting operation of the tool.

Although the alignment guide 115 can be configured in a variety of shapes, in the present instance, the alignment guide is an elongated flat bar positioned parallel to the cutting blade 102 and in close proximity to the cutting blade. The guide 115 preferably is more rigid than the cutting blade, and preferably is substantially rigid relative to the cutting blade. In this way, the alignment guide supports the cutting tool limiting the deflection of the cutting blade toward the guide.

During a procedure, the alignment guide operates as follows. As described above, the surgeon views the monitor to properly align the surgical tool to perform the cut. After the surgical tool is aligned, the surgical tool is anchored to the bone by driving the tool toward the patient bone to anchor the pins 116 in the bone. The surgical tool may include an internal hammering device to lock the anchoring pins 116 to the bone when the alignment is correct, or the surgical tool can simply include a contact portion, such as an anvil 118 that can be hammered to drive the pins 116 into the bone. As described below, during a cut, the guide 115 collapses. Accordingly, to anchor the pins into the bone, the guide 115 includes a brake or a lock to lock the guide in an extended position while the pins are anchored into the bone.

Once the guide 115 is anchored to the bone, the surgeon starts the tool and the cutting blade 102 is driven into the bone. The lock or brake on the guide is released to allow the guide to collapse during a cut. Specifically, the guide 115 is configured so that it can collapse or telescope as the saw is moved forward during the procedure. In other words, the pins 116 remain in engagement with the tissue (e.g. bone) and the guide 115 collapses as the saw move forward relative to the pins. In this way, the pins 116 anchor the cutting blade 102 as the cutting blade progresses through a cut.

Figure 5:
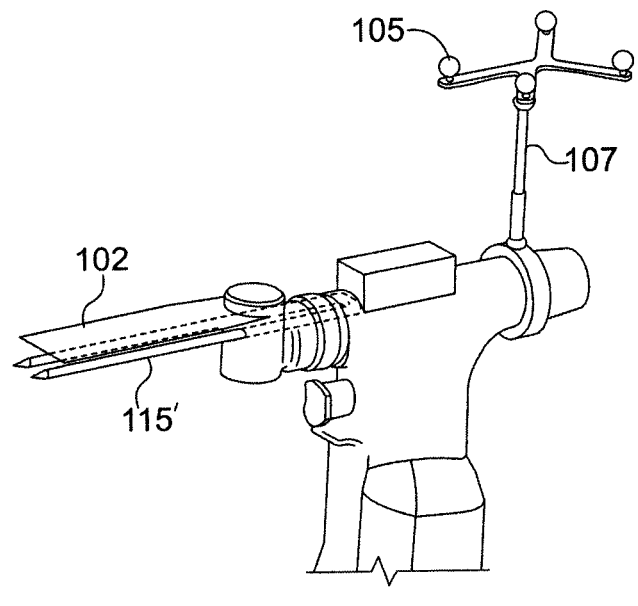
FIG. 5 is an alternative embodiment of the surgical tool illustrated in FIG. 4.
Figure 6:
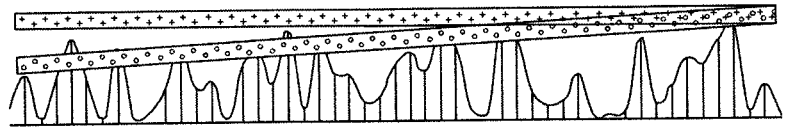
FIG. 6 is plot illustrating data regarding the surface roughness and surface waviness.

As described above, the alignment guide includes a flat bar and retractable pins. However, the configuration of the guide can vary based on a number of criteria, including, but not limited to design, friction and heat requirements, sterilization needs etc. For instance, rather than being an elongated flat bar, the guide may comprise a pair of elongated cylindrical rods spaced apart from one another. The ends of the rods may be pointed to facilitate anchoring the guide into the bone, as shown in FIG. 5.

Navigable Marker

As described previously, the OR computer 80 may display a virtual model of the portion of the patient on which the procedure is to be performed. Further still, the location of the patient may be registered to correlate the position of the patient with the virtual model. In previous descriptions, the virtual model of the patient was utilized to guide the surgeon in manipulating the surgical tool to perform the surgery. Alternatively, the virtual model of the patient may be used to guide the surgeon in marking the operation site. The marking can then be used alone or in combination with the guided freehand system described above.

Figure 13:
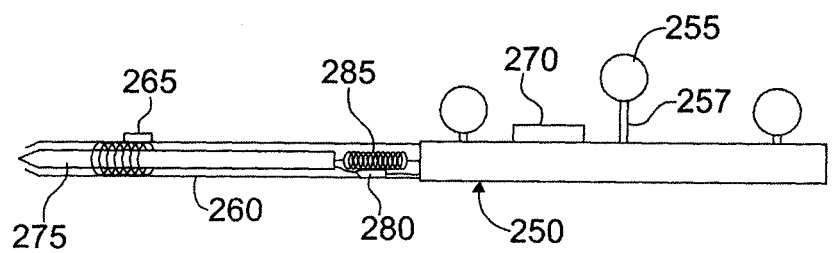
FIG. 13 is a diagrammatic illustration of a navigable marking pen.

Referring to FIG. 13, a navigable marking pen 250 is illustrated. The navigable marking pen 250 includes one or more elements for detecting the position and orientation of the marker. For instance, the marking pen may include a reference frame 257 and a plurality of position markers 255 similar to the frame 107 and position markers 105 described above in connection with the surgical tool. The marking pen 250 can be guided by viewing the display of the OR computer 80 as described above in connection with operation of the surgical tool 100. The marking pen 250 is guided to draw lines on the bone at the appropriate locations as identified on the virtual model.

The method for using the navigable marking pen 250 operates as follows. Prior to the procedure, a virtual model of the relevant portion of the patient is created as discussed above. The surgeon analyzes the virtual model to determine the procedure to be performed and identifies the portion of the patient to be resected or otherwise operated upon during the procedure. For instance, in the instance of implanting a prosthetic device, a femoral prosthetic may be implanted as previously described. The surgeon selects the appropriate prosthetic and aligns a model of the prosthetic over the operation site. Based on the model of the prosthetic and the alignment, the Pre-op computer 70 may identify the tissue to be resected during the procedure. Prior to the procedure, the patient is registered as described previously, so that the patient position corresponds to the virtual model. The OR computer 80 displays the virtual model along with a model of the navigable marking pen and an indication of the tissue to be resected. As the surgeon manipulates the marking pen 250, the position detection device 120 detects the movement of the marking pen and provides data to the OR computer so that the model of the marking pen moves on the screen relative to the patient model in real time. Accordingly, the surgeon manipulates the marking pen so that the model of the marking pen aligns with the portion of the virtual model indicated for resection. The surgeon manipulates the marking pen 250 so that the model of the marking pen traces the area of the virtual model identified for resection or other procedure (such as drilling). In this way, the virtual model provides a guide for guiding the surgeon to mark the appropriate areas on the patient on which the procedure is to be performed. The surgeon may then simply perform the procedure freehand using the markings on the patient as a guide or the surgeon may perform the procedure using the markings and also using freehand navigation assistance as described above.

FIG. 13 also illustrates another potential improvement, in that the marking pen 250 may include a retractable pen that retracts when the marking pen is not aligned with the proper area on the patient. By retracting, it is much less likely that the surgeon may erroneously mark an incorrect area.

As shown in FIG. 13, the marking pen 250 includes a hollow housing 260 having a generally open forward end. A displaceable pen 275 is disposed within the hollow housing 260. The pen is displaceable between an extended position and a retracted position. In the extended position the tip of the pen extends from the housing so that the tip of the pen can be used to mark a surface. In the retracted position the pen is retracted into the housing so that the forward tip of the pen is within the housing so that the pen can not be used to mark a surface.

A spring 285 connected to the pen 275 biases the pen toward the retracted position. An actuator 280, such as a solenoid is operable to extend the pen forwardly against the bias of the spring. Specifically, when the solenoid is energized, the solenoid drives the pen to the extended position. When the solenoid is de-energized, the spring 285 retracts the pen into the housing. Alternatively, the solenoid can be configured to drive the pen in both directions, i.e. the solenoid can drive the pen forwardly and rearwardly as desired.

The marking pen 250 is in communication with the OR computer 80 to receive signals indicating whether the pen 275 should be extended or retracted. The marking pen may include a wired connection to the OR computer, however, in the present instance, the OR computer 80 includes a transmitter, and the marking pen includes a wireless receiver for receiving signals from the computer. The marking pen 250 includes a processor 270 for receiving the signals from the computer and controlling the extension and retraction of the pen 275 in response to the signals. Specifically, the processor 270 controls the operation of the solenoid to selectively energize and de-energize the solenoid in response to signals received from the OR computer.

The operation of the retractable marking pen 250 is similar to the operation described above. However, the OR computer correlates the data from the virtual model with the data regarding the position of the marking pen. If the OR computer determines that the marking pen is positioned over a portion of the patient that should be marked, the computer transmits a signal to the marking pen 250 indicating that the pen should be extended. The marking pen receives the signal and the processor 270 controls the solenoid, thereby energizing the solenoid to extend the pen tip 275. If the OR computer determines that the marking pen is position over a portion of the patient that is not to be marked, the computer transmits a signal to the marking pen indicating that the pen should be retracted and the processor control the solenoid to retract the pen. Alternatively, the processor may be configured so that the solenoid is energized only as long as the controller receives a signal indicating that the pen should be extended. In this way, the OR computer sends a signal to the marking pen as long as the computer determines that the marking pen is over a portion to be marked. As soon as the computer determines that the marker is over an area that is not to be marked, the computer ceases sending a signal to the marking pen. The processor then de-energizes the solenoid to retract the pen in response to the lack of signal.

As can be seen from the foregoing, the marking pen 250 can provide an accurate and efficient method for marking cut lines and other marking lines for performing a procedure. Prior to the procedure, the surgeon may utilize the guidance system to manipulate the marking pen by aligning the model of the pen with the area of the virtual model to be operated on. While the surgeon maintains alignment of the virtual pen with the portions of the model indicated as proper marking lines (such as the outline of a prosthetic), the OR computer sends a signal to the marking pen indicating that the pen element 275 should be extended. As the surgeon maintains the virtual pen aligned on proper parts of the virtual model, the marking pen 250 marks the patient. If the surgeon manipulates the pen so that the virtual pen moves out of alignment with the proper parts of the virtual model, the OR computer sends a signal to the marking pen (or ceases sending a signal to the pen as described above) and the pen tip 275 retracts into the housing so that the pen stop marking the patient. In this way, the surgeon controls the retraction of the pen by maintaining alignment of the virtual pen with the portion or portions of the model the were identified during the pre-operative analysis as portions to be marked.

Tool Registration Head

An important step during navigated surgery is the accurate registration of the surgical tools. If a tool is not properly registered the navigation of the tool will be flawed leading to errors during the procedure.

Figure 14:
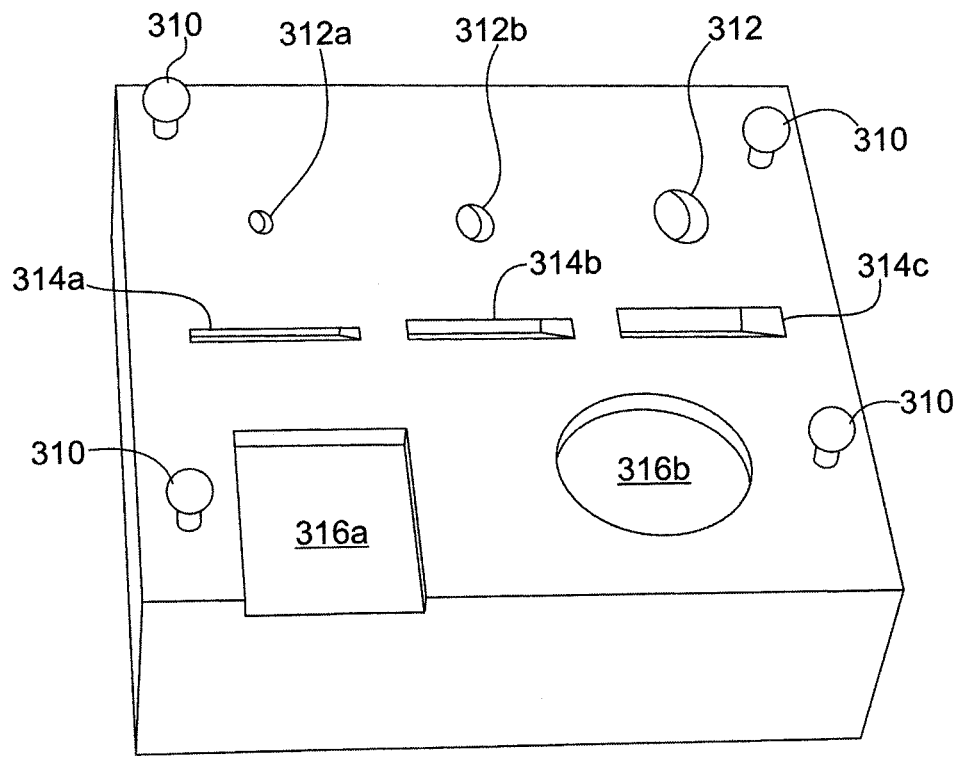
FIG. 14 is a registration block for registering tools of a surgical instrument.

Referring to FIG. 14 a tool registration head 300 is illustrated. The registration head 300 is configured to cooperate with a plurality of tools 320 that are configured to be mounted in a plurality of sockets in the head. The sockets are configured so that each socket cooperates with a particular tool. In this way, the system identifies the tool type in response to a determination of the socket into which the tool is mounted. For instance, the registration head 300 may include first 312, second 314 and third sockets 316, each having a different configuration. A first tool is configured to mate with the configuration of the first socket, a second tool is configured to mate with the configuration of the second socket and a third tool is configured to mate with the configuration of the third socket. Each socket further includes a sensor indicating whether a tool is registered in it or not. If the sensor in the first socket indicates the presence of a tool, the system determines that the first type of tool is mounted in the registration head. Similarly, if the sensor in the second or third socket detects the presence of a tool, the system identifies the tool as being the second or third type accordingly.

Alternatively, rather than including a sensor in each slot, the registration block may include a plurality of detection element 310, such as reflective spheres, as shown in FIG. 14. The location of each slot relative to the detection elements is known. Therefore, by inserting the surgical tool into the appropriate registration slot, the position of the surgical tool relative to the registration block is known. Based on this position data, the processor is able to determine which registration slot the surgical instruments was inserted into, thereby identifying the instrument.

Additionally, as described above, the various registration slots may vary depending on the type of instrument used, as well as the size of the instrument. For instance, in FIG. 14, the registration block include several holes of varying size 312*a, b,b*. By inserting the instrument into hole 312*a*, the system detects that the instrument is a pointer or drill bit or a diameter corresponding to hole 312*a*. Similarly, slots 314*a,b,c* are used to indicate that the instrument is a saw of a particular thickness.

Further, the sockets 310 and the tools may also be configured so that each tool will only mount in a particular orientation. In other words, each tool fits into a particular socket in a particular orientation. In this way, by simply identifying which socket a tool is mounted in, the system can determine the tool type and orientation.

The registration head is in communication with the OR computer 80 or the position detection device 120 so that the registration head can communicate signals to the system indicative of the tool registered in the head. The system may maintain a data file for each tool type indicating the profile and operating parameters for each tool. In this way, when the system identifies the tool registered in the head 300, the system has the relevant data regarding the size, configuration etc. of the tool so that the system can monitor the position of the tool accordingly.

Identifying Regions of Waste Material

As described previously, the present system 50 could be utilized to perform guided freehand surgery in which a model of the patient is provided, along with a model of the surgical tool and the models can be used to guide the surgeon during the actual procedure. For instance, the patient model may include a portion identified as tissue to be resected. The system tracks the movement of the surgical tool 100, so that when the surgeon moves the tool, the system displays the movement of the tool in real time on the monitor. In this way, the surgeon can align the tool with the patient by aligning the model of the tool with the portion of the patient model identified for resection. In this way, the surgeon can follow the onscreen guidance to resect a portion of tissue.

When resecting a portion of a bone a surgeon may cut more rapidly and aggressively when the cutting tool is relatively far from the boundary of the area to be resected. As the surgeon approaches the boundary of the resection area, the surgeon may slow the pace of cutting to ensure that the resection remains within the desired boundaries. To help the surgeon readily assess the proximity to the resection boundary, the system may provide indicators and warnings to the surgeon as the surgeon approaches the boundary. Further still, the system may be configured to control the operation of the surgical tool 100 in response to the proximity of the tool to the resection boundary.

As described above, the system provides for the pre-operative analysis of a patient model and the identification of the tissue to be resected. After the portion of the tissue to be resected is determined, the system may analyze the data for the model and identify the boundary for the resection. The tissue to be resected may then be identified with a plurality of colors based on the relation to the resection boundary.

For instance, the portion of the tissue that is not to be removed may be illustrated in red. A portion of the tissue that is to be resected that is relatively close to the resection boundary may be illustrated in yellow. The remainder of the tissue to be resected may be illustrated in green. In this way, as the surgeon views the model during a procedure the surgeon may cut rapidly and aggressively while the system indicates the tool is operating on tissue in the green zone. As the surgeon approaches the resection boundary, the model illustrates the tool as operating on tissue in the yellow zone. This serves as an indication to the surgeon to proceed more slowly as the tool approaches the resection boundary. In this way, the system provides a readily identifiable graphical display that informs the surgeon of the proximity of the surgical tool to a resection boundary. Similarly, the system can be used to identify the proximity of the surgical tool to sensitive anatomical structures, such as nerves, vessels, ligaments etc. The anatomical structures can be illustrated in red and the tissue proximate the structures can be identified in yellow as an indicator to the surgeon that the cutting tool is getting close to the sensitive structure.

In addition to providing a graphical indication of the proximity to a resection boundary, the system may provide a graphical and/or audible warning to the surgeon. For instance, as the system detects the surgical tool approaching the area proximate the resection boundary (i.e. the yellow zone), the system may display a graphical warning on the monitor 85 in addition to illustrating the surgical tool in a yellow zone of tissue on the model. Alternatively or in addition to the graphical warning, the system may provide an audible warning indicating that the cutting tool is approaching the desired boundary. The system may provide yet another warning in the event the cutting tool is detected at or beyond the desired boundary. In other words, if the surgical tool enters the red zone the system may provide a further warning.

The system may also be configured to control the operation of the surgical tool in response to a determination of the position of the surgical tool relative to the desired boundary. Specifically, if the system determines that the tool is positioned within the tissue to be resected that is not proximate the boundary (i.e. in the green zone), the system may allow the surgical tool to controlled as desired by the surgeon. If the system determines that the tool is positioned within the tissue to be resected that is proximate the boundary (i.e. the yellow zone), the system may reduce or attenuate the operation of the surgical tool. For instance, if the tool is a saw, and it enters the yellow zone, the system may slow down the reciprocation or revolution of the saw as it moves proximate the resection boundary. Further still, if the system detects that the tool is positioned at the boundary or on tissue that is not to be resected or operated on, the system may control the surgical tool by completely stopping the tool. Although the system may automatically control the operation of the surgical tool, the system includes an override function that allows the surgeon to override the control of the tool. In this way, if the surgeon determines that a portion of tissue should be resected that was not identified for resection during the pre-operative analysis, the surgeon can override the system and resect the tissue during the procedure.

Yet another feature provided by identifying operating parameters for different areas of tissue is the ability to automatically vary the view displayed on the monitor during a procedure. For instance, when the system detects the surgical tool in a first area of tissue, the monitor may display a first view, whereas, when the system detects the tool in a second area of tissue, the monitor may display a second view. Specifically, if the system detects the surgical tool in the green zone portion of tissue, the system may display a wide angle or low zoom view so that the surgeon can view more of the area being operated on. As the tool enters the yellow zone, the system may change the view to a more magnified view so that the surgeon can see the details of the cut more clearly as the tool approaches the resection boundary. If the surgeon prefers different views than the ones automatically presented by the system, the surgeon can manually select a different view. Additionally, the system may query the surgeon as to whether the selected view should be the default view for the particular zone of tissue. If the surgeon responds in the affirmative, the system changes the default view for the particular user, so that the new view is displayed for the user when the cutting tool enters the corresponding type of tissue. In this way, the system can automatically change the view based on detected characteristics of a procedure and user preferences.

Another feature that may assist in guide the surgeon during a procedure relates to the representation of the tool of the surgical instrument. For instance, in the situation of a cutting tool, such as a saw, the cutting tool is a generally flat rectangular element. If the plane of a cut is illustrated by a line through a portion of tissue, it may be difficult to assess the angle of the cutting blade to ensure that the cutting blade is aligned with the plane of the appropriate cut. Accordingly, the cutting blade may be illustrated as an oval on the display. The shape of the cutting blade then depends on the angle of the cutting blade relative to the proper plane. If the cutting blade is aligned properly the cutting blade will look similar to a line. As the cutting blade is twisted relative to the proper cutting plane, the cutting blade appears more rounded and oval. In this way, the variation between the angle of the cutting blade and the angle of the proper cutting plane is readily apparent based on the ovality of how the cutting tool appears on the display.

Registration Pointer with Surface Contact Detection

As previously described, when registering the position of the patient prior to a procedure, a portion of the patient is scanned to identify one or more anatomical landmarks or features. Such features or landmarks are utilized to correlate the patient position with the virtual model created for the patient. One method for acquiring the registration data utilizes a navigational pointer that the surgeon traces over portions of the patient. However, when the surgeon is tracing the surface, the tip of the pointer may come out of contact with the surface of the patient. This is particularly true when tracing over soft tissue or when tracing along curved surfaces. If the pointer is not in contact with the surface of the relevant portion of the patient the resulting data points will be erroneous.

To improve the accuracy of the data collected during registration, the system may include a pointer that incorporates a surface contact detection element. If the pointer is out of contact with the surface of the relevant portion of the patient, the points are ignored during the registration analysis.

Figure 15:
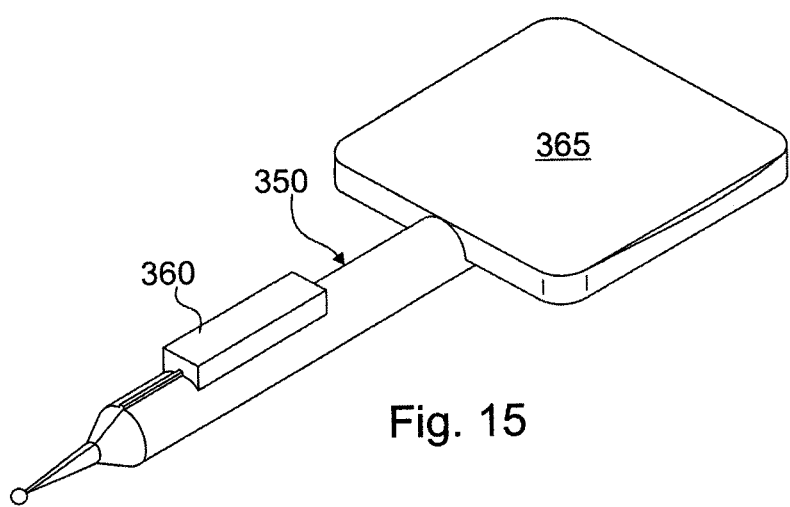
FIG. 15 is a registration pointer operable in connection with the surgical suite illustrated in FIG. 1 or FIG. 3.

Referring to FIG. 15 an improved registration pointer is designated 350. The pointer is an elongated element having a tip configured to contact the relevant portion of a patient. The pointer 350 is operatively linked with the position detection device 120. The operative link may be a wireless connection in which the pointer includes a wireless transmitter. Alternatively, the pointer may be connected directly to the detection device via a cable.

The pointer includes a sensor 360 for detecting whether the tip of the pointer is in engagement with the patient or whether the tip of the pointer is spaced apart from the patient. One possible sensor 360 is an impedance sensor. Alternatively, the sensor may be a simple force transducer. The pointer 350 includes a circuit 365 for analyzing the signal from the sensor and determining whether the pointer is in contact with the patient surface based on the signal from the sensor. The data for the point or points in which the pointer was out of contact with the patient surface are not utilized during the registration process. Specifically, the pointer circuit may identify valid and invalid data by various means, including a first method in which the pointer communicates the relevant data to the position detection device 120 via a wired or wireless connection. Alternatively, the pointer circuit may control the position tracking elements so that the pointer is out of view of the position detection device 120 when the pointer 350 is out of contact with the patient surface.

In the instance in which the pointer circuit communicates directly with the position detection device, the pointer circuit evaluates whether the pointer is in contact with the patient based on the signal received from the sensor 360. If the circuit determines that the pointer is out of contact, the circuit communicates a signal to the position detection device 120 indicating that the data points are invalid. In this way, as long as the pointer remains out of contact with the patient surface, the position detection device receives a signal from the pointer indicating that the points are invalid and should be ignored.

Alternatively, the pointer may control the position detection elements to essentially make the pointer disappear from view of the position detection device 120 when the pointer is out of contact. Since the pointer is out of view when it is out of contact with the patient, no data is collected while the pointer is out of contact. The steps for rendering the position detection elements out of view of the detector varies depend on the type of detection element. For instance, as described previously, the position detection device may operate in conjunction with passive and active markers. An active marker is a marker that transmits an infrared signal to the detection device and the position of the marker is identified by triangulating the received signal. Accordingly, to control the active marker(s), the pointer circuit 365 controls the active markers by turning off the active markers so that they no longer emit an infrared signal when the pointer is out of contact with the relevant portion of the patient. While the emitter ceases emitting infrared light, the marker is hidden from the position detection device 120 so that the registration points are not detected.

If the markers on the pointer are passive elements, the markers are detected by detecting the infrared light reflected back to the position detection device 120. In order to hide such passive markers the pointer circuit may be used to control one or more elements including a displaceable opaque surface and an electronically/chromatically actuated effect to disable the infra-red reflectivity of the ball.

Automatic Selection of View

During a procedure, the surgeon is able to manipulate the view of the patient model to view the model from any desired angle or magnification. Furthermore, the system may be configured to automatically select the appropriate view based on the status of the procedure and information regarding the surgeon's preferences.

As described above, the system is operable to track the position of the surgical instrument 100 and correlate the position of the tool relative to a virtual model of the patient. Additionally, the virtual model may indicate the portions of the patient that are to be operated on. For instance, the virtual model may identify the boundaries of the tissue to be resected during a procedure. The tissue to be resected may include a number of portions along a number of planes.

When resecting the various portions it may be desirable to modify the view of the virtual model displayed on the monitor. For instance, when cutting along a first plane it may be desirable to view the virtual model from a first perspective, and when cutting along a second plane it may be desirable to view the virtual model from a second perspective. Accordingly, the system tracks various data regarding the status of a procedure, including, but not limited to the following: the position of the surgical tool relative to the tissue to be resected and the orientation of the surgical tool relative to the tissue to be resected. Based on the position and orientation of both the tissue and the surgical tool, the system calculates which surface is about to be cut during the procedure.

Figure 10:
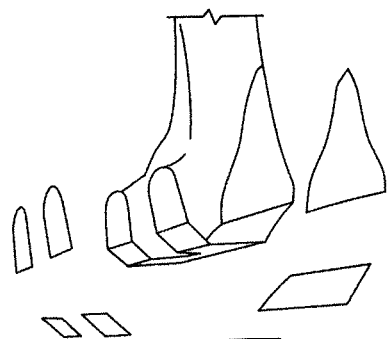
FIG. 10 illustrates the femur cuts for a total knee replacement procedure.
Figure 11:
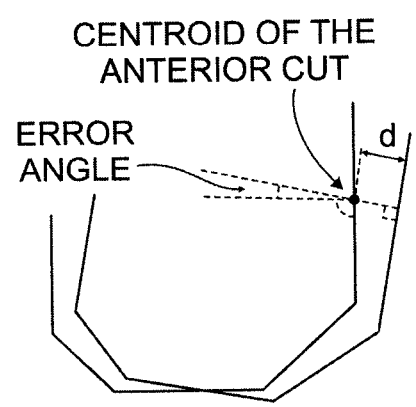
FIG. 11 is a diagram illustrating the error angle for bone cuts in a total knee replacement procedure.

The system is pre-programmed so that certain views are shown by default for certain cuts. For instance, returning to the example of resecting a femur in preparation for a femoral prosthetic for a TKR procedure, several surfaces are to be cut, as shown in FIG. 10. Each surface may be best viewed from a different perspective during the procedure. When cutting the anterior surface of the medial condyle a first view may be desirable, whereas when cutting the anterior surface of the lateral condyle a second view may be desirable. Accordingly, the system sets a pre-defined first view for viewing the virtual model when the anterior surface of a medial condyle is resected. Similarly, default views can be defined for a number of common resection procedures. When the system determines the cut to be performed, the system determines the best match for the cut and displays the default automatically without the intervention of the surgeon.

Further, the system can be configured to account for the preference of each user. Specifically, a surgeon may desire a different view than the default view for a particular resection step or cutting plane. The system allows the surgeon to override the default selection and specify the view for a particular cut. The system stores the information regarding the desired view for the particular cut for the particular surgeon and uses the view as the default view in the future when the system determines that a similar cut is to be made. The system tracks the user preference based on the user logged into the machine.

In addition to automatically changing views based on certain pre-defined presumptions, the system can be programmed to identify the particular views to be displayed during a procedure. For instance, during the pre-op analysis of the patient's model, the surgeon may identify the view to be displayed for each portion of the procedure. For example, during the resection of the bone for a TKR, the surgeon may identify the view to be displayed for each of the different cuts to be made during a procedure. These preferences can be saved to the profile for the user and used in other future procedures, or the information can simply be used for the particular procedure. As the procedure proceeds, the system tracks the surgical tool, determines the surface that is going to be cut and displays the virtual model using the view chosen for the surface during the pre-op procedure.

Figure 3:
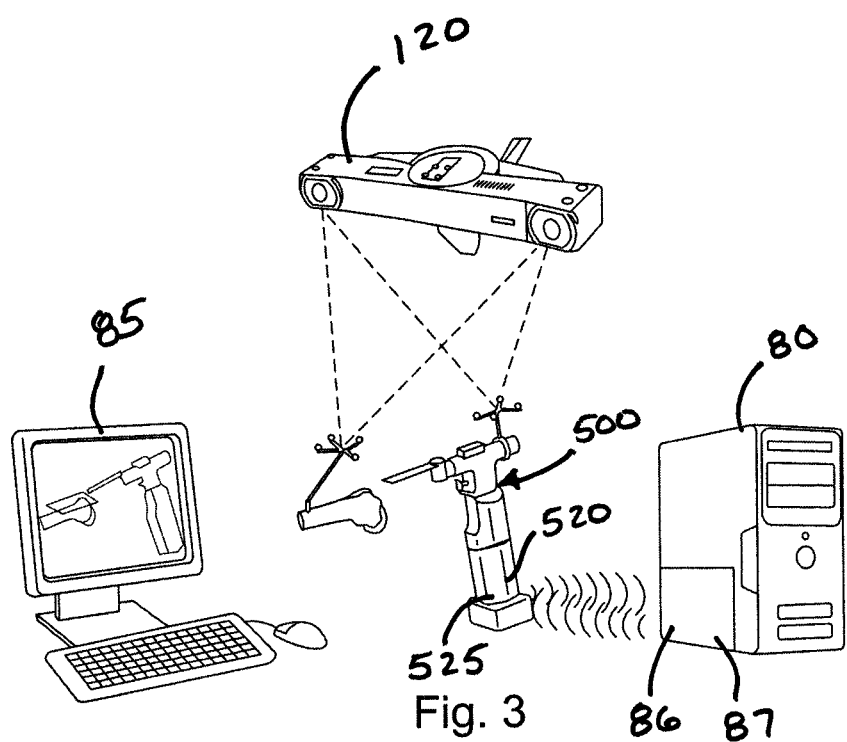
FIG. 3 is an alternative diagrammatic view of a computer assisted surgical suite.

Referring now to FIG. 3 another embodiment of a computer aided system with a surgical instrument 500 is illustrated. The surgical instrument 500 is operable to assist in automated surgery in a surgical suite as discussed above in connection with the surgical instrument 100 described above. For instance, as described above, the system may include position detection device 120 that operates to detect the position of the surgical instrument 500 relative to the patient. In the present instance, the position detection device detects the position of one or more markers 505 on the surgical instrument and one or more markers connected to the patient. In addition to the aspects, the surgical instrument 500 incorporates a number of features on the instrument itself so that the instrument can be used to perform a number of functions. Additionally, the surgical instrument may incorporate wireless communication with the OR computer 80.

Referring to FIG. 3 the surgical instrument 500 includes a tool, such as a saw 510, a microcontroller 515 for monitoring and controlling operation of the tool 510, and a wireless unit 520. The instrument 500 also includes an antenna 525. The wireless unit 520 and antenna 525 allow the instrument to send data to the OR computer 80 regarding multiple status parameters, such as blade bending, saw speed and battery charge. In addition, the OR computer 80 includes a wireless unit 86, such as a bluetooth wireless element, and an antenna 87. The wireless unit 86 and antenna 87 allow the OR computer to send and receive data wirelessly to and from the surgical instrument 500.

As described previously, the OR computer may be used to guide the surgeon's operation of the surgical tool during a procedure. For instance, the system may track the position of the surgical tool in real time and turn on or off the surgical tool depending on whether the tool is in proper alignment. For instance, if the system detects that the surgical tool is adjacent an area to be resected, the system may send a signal wirelessly to the tool. If the tool does not receive such a signal, the tool will not operate. Specifically, the surgical tool may have a manual switch that the surgeon can manually turn on to operate the tool. However, the tool will only run if both the manual switch is switched to the on position and if the tool also receives a signal indicating that the tool is properly positioned to perform a procedure. If either the surgeon switches the tool off or if the tool does not receive a signal indicating that the tool is properly positioned, the tool will not turn on for cutting.

As described above, the tool 500 may receive signals wirelessly to control operation of the tool. In addition to signals controlling the on/off function of the tool, signals may also be used to control other operation of the tool. For instance, the tool may receive signals that operate to control the speed of the tool. For example, as described above, the system may track the position of the tool, so that the system can track whether the tool is adjacent a cutting boundary for a desired procedure. As the tool approaches the boundary, the system may send a signal to the tool indicating that the tool should be attenuated to reduce the speed of the tool. The circuitry in the tool 500 then attenuates the operation of the tool in response to the wireless signal.

As described above, the surgical tool 500 may be controlled in response to wireless signals from the OR computer 80. In addition, operation of the system may be controlled by signals from the surgical tool, which in this instance are wireless signals. For instance, the surgical tool may include various actuators, such as buttons, a joystick or a mouse ball. The operation of such actuators may be used as input signals to control operation of the OR computer. For example, operation of a joystick on the surgical tool 500 may send signals to the OR computer 80, causing the graphics displayed on the display 85 to scroll in a particular direction. Similarly, one or more buttons can be programmed to send wireless signals to change the perspective or magnification of the graphic being displayed.

Figure 16:
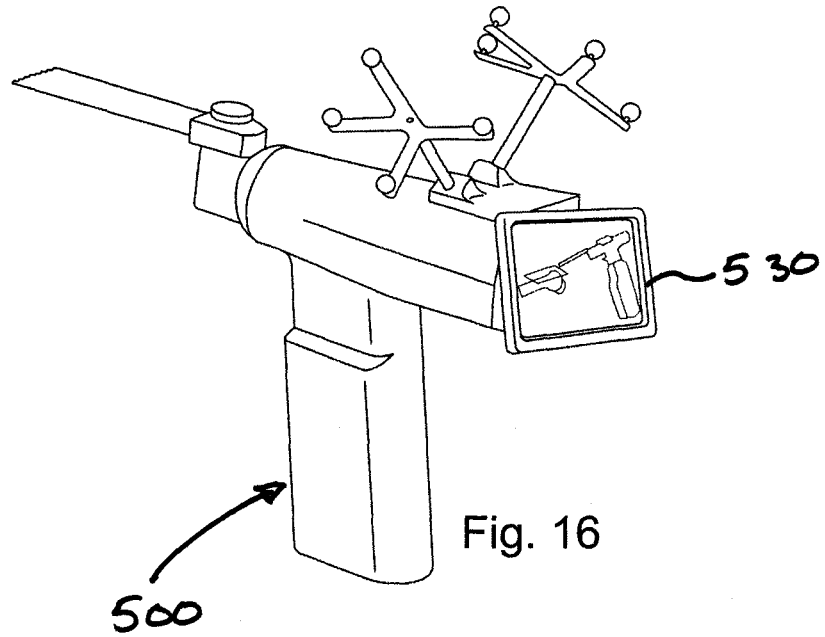
FIG. 16 is an alternative embodiment of a surgical tool operable in connection with the surgical suite of FIG. 1 or FIG. 3.
Figure 17:
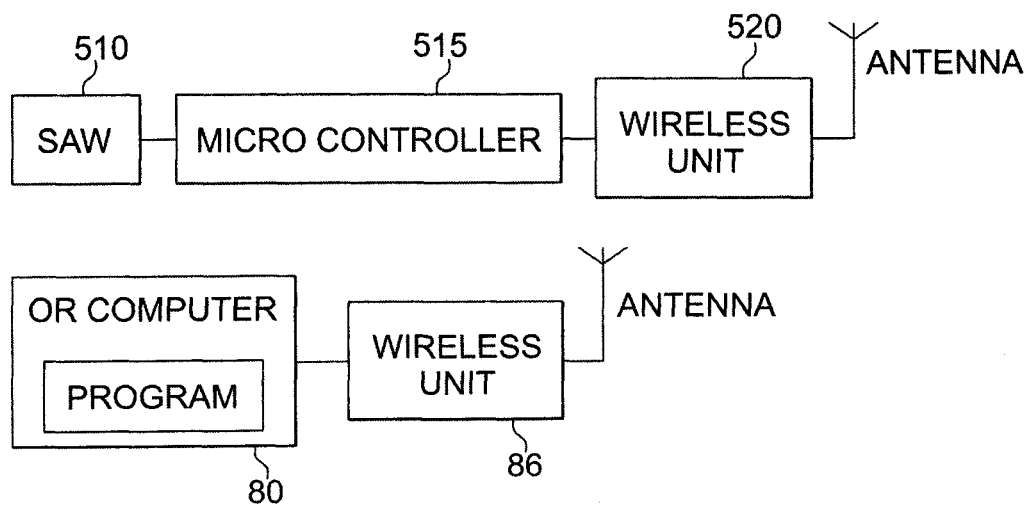
FIG. 17 is a block diagram of the wireless features of the surgical suite illustrated in FIG. 3.

In addition to including actuators, the surgical tool 500 may include a display 530 or view screen as shown in FIG. 16.

Specifically, as described above, the tool may include a wireless connection for receiving data from the OR computer 80. The OR computer may transmit graphics data to the tool so that the display 530 may display the same graphics as are displayed on the main OR computer 80 display 85. Alternatively, the display 530 may display an alternate view to the graphic being displayed on the OR computer display 85. In this way, the display screen 530 may be used to guide the surgeon during a procedure in the same way that the OR computer display 85 may be used to guide the surgeon.

As previously discussed, preferably a pointer is provided for identifying reference points on the patient. Although the pointer has been described as a separate element, the pointer may be integrated into the surgical tool. For instance, since the configuration of the saw blade is known, the tip of the saw blade can operate as a pointer. Alternatively, a dedicated pointer may be incorporated onto the surgical tool. It may be desirable to configure the pointer so that it can be extended and retracted as necessary so that the pointer can be readily used, while not interfering with the operation of the cutting tool during a procedure.

The operation of the pointer element may operate in conjunction with an actuator on the surgical tool. For instance, the tool may include a button for indicating that the pointer is positioned at a reference point. When the surgeon positions the pointing element at a point to be registered, the surgeon simultaneously presses the button, sending a signal to the OR computer indicating that the point is to be registered as a reference point. The OR computer detects the position of the surgical tool as determined by the position detection device, and stores the data regarding the location of the reference point. In this way, the OR computer stores information regarding the position of the surgical tool in response to actuation of the button on the surgical tool.

Cutting/Filing Blade

Figure 18:
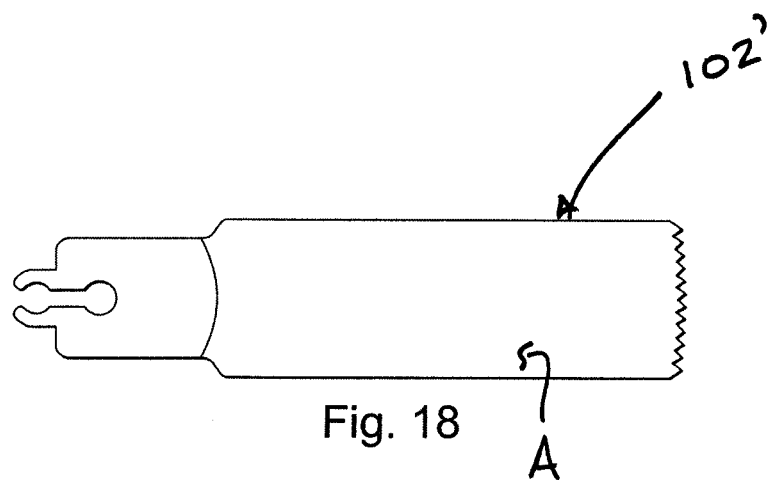
FIG. 18 is a top view of an alternative cutting blade operable in connection with a surgical saw.
Figure 19:
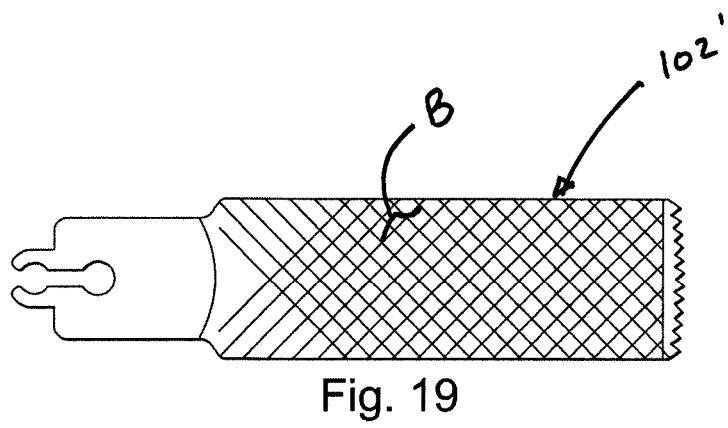
FIG. 19 is a bottom view of the cutting blade illustrated in FIG. 18.

Referring to FIGS. 18-19 an alternate cutting blade 102' is illustrated. The cutting blade 102' has alternate surfaces on the body of the blade. The first side A is smooth as with a conventional blade; the opposite side B of the blade is formed with a plurality of cutting surfaces to form a filing surface. The smooth side is used against the useful (remaining) bone when pure edge cutting is required. The blade is flipped (e.g. by turning the oscillatory saw head 180 degrees) when cutting and filing (or filing only) is required against the useful remaining bone. The bide then acts as a navigated file but with a cutting edge as well. The cutting edge/tip and filing surface features combine to make the navigated saw more effective for advanced navigated freehand bone cutting. The filing surface can act as a navigated testing plane to measure alignment accuracy of the surface and refine it by filing.

It will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

The invention claimed is:

1. A method for performing a navigated freehand computer assisted surgical procedure on a knee of a patient, comprising the steps of:
    creating a three dimensional representation of a knee portion of a patient to which the procedure is to be performed;
    identifying a portion of the three dimensional representation corresponding to a bony portion of knee to be resected;
    identifying the orientation of a cutting plane for resecting the identified bony portion;
    displaying the three dimensional representation during the surgical procedure,
    wherein the step of displaying comprises:
    displaying the portion to be resected in a first color;
    displaying a boundary adjacent the portion to be resected in a second color that is different from the first color; and;
    displaying a portion of tissue adjacent the boundary, which is not to be resected, in a third color, which is different from the first and second colors;
    performing the navigated freehand surgical procedure using a navigated freehand surgical tool to resect the bony portion of the knee;
    tracking the real time position and orientation of the freehand surgical tool relative to the cutting plane; and
    displaying an indicator of the variation between the cutting plane and the real time position of the navigated freehand surgical tool, wherein the indicator is based upon the identified orientation of the cutting plane and the real time position of the navigated freehand surgical tool.

2. The method of claim 1 comprising the step of deleting a portion of the three dimensional representation corresponding to tissue being removed during the surgical procedure.

3. The method of claim 2 wherein the step of deleting a portion of the three dimensional representation is repeatedly updated in real time.

4. A method for controlling a navigated freehand surgical tool during a surgical procedure, comprising the steps of:
    creating a three dimensional representation of a portion of a patient to which a procedure is to be performed;
    identifying a portion of the three dimensional representation corresponding to a portion of tissue onto which a surgical procedure is to be performed;
    identifying the position and orientation of a desired cut plane for resecting the identified portion;
    cutting the portion of the patient by performing a navigated freehand surgical procedure;
    tracking the position and orientation of the surgical tool during the cutting step; and
    providing an indicator of the variation between the tracked position, orientation and path of the freehand surgical instrument from the tracking step relative to the desired cut plane;
    automatically controlling in real time the operation of the surgical tool in response to the proper position and alignment of the surgical tool relative to the patient.

5. The method of claim 4 wherein the surgical tool is a motorized cutting tool and the step of controlling the operation comprises the step of turning off the surgical tool.

6. The method of claim 4 wherein the surgical tool is a motorized cutting tool and the step of controlling the operation comprises the step of slowing the speed of the surgical tool.

7. The method of claim 4 comprising the step of manually overriding the automatic control of the surgical tool.

8. The method of claim 1 wherein the indicator is a graphical display indicative of the variation between the cutting plane and the plane to be cut.

9. The method of claim 8 wherein the indicator provides a representation of the cutting plane wherein the shape of the representation of the cutting plane varies according to the deviation between the cutting plane and the real time position and orientation of the navigated freehand surgical tool.

10. The method of claim 1 comprising the steps of providing a graphical display of the plane to be cut and a graphical display of the cutting plane.

11. The method of claim 10 wherein the step of providing a graphical display of the cutting plane comprises providing a real-time graphical display indicative of the orientation of the cutting plane relative to the plane to be cut.

12. A method for planning and performing a navigated freehand computer assisted surgical procedure on a joint of a patient, comprising the steps of:
creating a three dimensional representation of a portion of a joint to which the procedure is to be performed;
identifying a portion of the three dimensional representation corresponding to a bony portion of the joint to be resected;
identifying a position and an orientation of a plane to be cut for resecting the identified portion;
displaying on a view screen a pre-operative three dimensional representation of the bony portion of the patient based on the creating, identifying a portion and the identifying a position and an orientation steps;
performing a navigated freehand surgical procedure using a surgical tool to resect the identified portion of the joint;
tracking the position and orientation of the surgical tool relative to the portion of the joint;
providing an indicator on the view screen of the alignment between the position and orientation of the surgical tool to the identified plane to be cut, wherein the position and orientation of the surgical tool is determined based on the step of tracking; and
updating the indicator in real time during the performing step.

13. The method of claim 12 wherein the step of providing an indicator comprises the step of providing a graphical display on the view screen that is indicative of the alignment of the cutting plane relative to the identified plane to be cut.

14. The method of claim 13 wherein the step of providing a graphical display comprises providing a real-time graphical display indicative of the orientation of the cutting plane relative to the plane to be cut.

15. The method of claim 12 wherein the step of providing an indicator comprises the step of illustrating on the view screen a representation of the cutting plane wherein the shape of the representation of the cutting plane varies according to deviation between the cutting plane and the identified plane to be cut.

16. The method of claim 12 comprising the step of automatically changing the angle from which the three dimensional representation is viewed in response to the step of tracking.

17. The method of claim 16 comprising the step of identifying the angle from which the three dimensional representation is viewed based on the orientation of the cutting tool relative to the portion of the patient.

18. A method for performing a computer assisted surgical procedure, comprising the steps of:
creating a three dimensional representation of a portion of a patient to which a prosthetic implant procedure is to be performed;
identifying a portion of the three dimensional representation corresponding to a portion of tissue to be resected to support a portion of a prosthetic implant;
identifying the position and orientation of a target surface for resecting the identified portion according to the prosthetic implant procedure to form a final surface shape;
displaying the three dimensional representation during a surgical procedure, wherein the step of displaying comprises:
displaying the portion to be resected in a first color;
displaying a boundary adjacent the portion to be resected in a second color that is different from the first color; and;
displaying a portion of tissue adjacent the boundary, which is not to be resected, in a third color, which is different from the first and second colors;
performing a surgical procedure in support of the prosthetic implant procedure using a freehand surgical tool to resect the portion of tissue;
tracking the location and orientation of the freehand surgical tool relative to the location and orientation of the target surface; and
providing an indicator to the user of the variation between the location and orientation of the freehand surgical tool and the location and orientation of the target surface from the tracking step.

19. The method of claim 18 comprising the step of deleting a portion of the three dimensional representation corresponding to tissue being removed during the surgical procedure.

20. The method of claim 19 wherein the step of deleting a portion of the three dimensional representation is repeatedly updated in real time.

21. The method of claim 18 wherein the indicator is a graphical display indicative of the variation between the cutting surface and the surface to be cut.

22. The method of claim 18 wherein the indicator provides a representation of the cutting surface wherein the shape of the representation of the cutting surface varies according to the deviation between the cutting surface and the surface to be cut.

23. The method of claim 18 comprising the steps of providing a graphical display of the surface to be cut and a graphical display of the cutting surface.

24. The method of claim 23 wherein the step of providing a graphical display of the cutting surface comprises providing a real-time graphical display indicative of the orientation of the cutting surface relative to the surface to be cut.

25. A method for performing a computer assisted surgical procedure using a navigated freehand saw, comprising the steps of:
creating a three dimensional representation of a portion of a patient to which a procedure is to be performed;
identifying a portion of the three dimensional representation corresponding to a portion of tissue to be resected;
identifying a position and an orientation of a surface to be cut for resecting the identified portion;
displaying on a view screen on the navigated freehand saw the three dimensional representation of the portion of the patient and a plane based on the identifying the position and the orientation step;
performing the surgical procedure with feedback from the displaying step while using the navigated freehand saw to resect the portion of tissue;
tracking the location and orientation of the navigated freehand saw relative to the patient; and
providing an indicator of the alignment between a cutting surface and the identified surface to be cut, wherein the cutting surface is the surface along which the navigated freehand saw is positioned to cut and is determined based on the step of tracking.

26. The method of claim 25 wherein the step of providing an indicator comprises the step of providing a graphical display on the view screen that is indicative of the alignment of the cutting surface relative to the identified surface to be cut.

27. The method of claim 26 wherein the step of providing a graphical display comprises providing a real-time graphical display indicative of the location and orientation of the cutting surface relative to the surface to be cut.

28. The method of claim 25 wherein the step of providing an indicator comprises the step of illustrating on the view screen a representation of the cutting surface wherein the shape of the representation of the cutting surface varies according to deviation between the cutting surface and the identified surface to be cut.

29. The method of claim 25 comprising the step of automatically changing the angle from which the three dimensional representation is viewed in response to the step of tracking.

30. The method of claim 29 comprising the step of identifying the angle from which the three dimensional representation is viewed based on the location and orientation of the cutting tool relative to the portion of the patient.

31. The method of claim 1 further comprising: displaying a portion of a pre-operative plan on a virtual model of a patient overlaid with the real-time navigated freehand procedure.

* * * * *